United States Patent
Garner et al.

(10) Patent No.: US 9,161,931 B2
(45) Date of Patent: Oct. 20, 2015

(54) DITHIOL COMPOUNDS AND TREATMENT OF PRESBYOPIA USING SAID COMPOUNDS

(71) Applicant: Encore Health, LLC, Roanoke, VA (US)

(72) Inventors: William Garner, Eastport, ME (US); Margaret Garner, Eastport, ME (US); Ronald D. Blum, Roanoke, VA (US)

(73) Assignee: Encore Health, LLC, Roanoke, VA (US)

( * ) Notice: Subject to any disclaimer, the term of this patent is extended or adjusted under 35 U.S.C. 154(b) by 0 days.

(21) Appl. No.: 14/170,116

(22) Filed: Jan. 31, 2014

(65) Prior Publication Data

US 2014/0243385 A1 Aug. 28, 2014

Related U.S. Application Data

(63) Continuation of application No. 12/390,928, filed on Feb. 23, 2009, now Pat. No. 8,647,612, and a continuation-in-part of application No. 12/267,260, filed on Nov. 7, 2008, now Pat. No. 8,697,109.

(60) Provisional application No. 61/033,870, filed on Mar. 5, 2008, provisional application No. 61/060,487, filed on Jun. 11, 2008, provisional application No. 61/077,186, filed on Jul. 1, 2008.

(51) Int. Cl.
*A61F 2/12* (2006.01)
*A61K 31/353* (2006.01)
*A61K 9/00* (2006.01)
*A61K 31/095* (2006.01)
*A61K 31/381* (2006.01)
*A61K 31/382* (2006.01)

(Continued)

(52) U.S. Cl.
CPC ............ *A61K 31/353* (2013.01); *A61K 9/0048* (2013.01); *A61K 31/095* (2013.01); *A61K 31/381* (2013.01); *A61K 31/382* (2013.01); *A61K 31/385* (2013.01); *A61N 5/0613* (2013.01); *A61N 2005/067* (2013.01)

(58) Field of Classification Search
CPC .................................................... A61K 9/0048
See application file for complete search history.

(56) References Cited

U.S. PATENT DOCUMENTS

| 3,238,224 A | 3/1966 | Ohara et al. |
| 3,855,240 A | 12/1974 | Mueller |

(Continued)

FOREIGN PATENT DOCUMENTS

| EP | 0 369 880 | 5/1990 |
| WO | WO 93/25166 | 12/1993 |

(Continued)

OTHER PUBLICATIONS

Al-Ghoul, K. J., R. K. Nordgren, A. J. Kuszak, C. D. Freel, M. J. Costello, and J. R. Kuszak. 2001. Structural evidence of human nuclear fiber compaction as a function of ageing and cataractogenesis. Experimental eye research 72: 199-214.

(Continued)

*Primary Examiner* — Carlos Azpuru
(74) *Attorney, Agent, or Firm* — Sterne, Kessler, Goldstein & Fox P.L.L.C.

(57) ABSTRACT

Dithiol compounds and derivatives thereof are disclosed. The agents are useful for treating ocular disease, especially presbyopia and cataract. Also disclosed are novel mercaptan compounds, particularly those including a photolabile protecting group, as well as methods of using the compounds for the prevention and treatment of ocular damage and disease.

20 Claims, 12 Drawing Sheets

(51) Int. Cl.
*A61K 31/385* (2006.01)
*A61N 5/06* (2006.01)
*A61N 5/067* (2006.01)

(56) References Cited

U.S. PATENT DOCUMENTS

| | | | |
|---|---|---|---|
| 4,210,667 A | 7/1980 | Sarges et al. | |
| 4,755,528 A | 7/1988 | DuPriest et al. | |
| 5,395,356 A | 3/1995 | King et al. | |
| 5,459,133 A | 10/1995 | Neufeld | |
| 5,465,737 A | 11/1995 | Schachar | |
| 5,466,680 A | 11/1995 | Rudy | |
| 5,476,515 A | 12/1995 | Kelman et al. | |
| 5,488,050 A | 1/1996 | Neufeld | |
| 5,503,165 A | 4/1996 | Schachar | |
| 5,527,774 A | 6/1996 | Giard | |
| 5,529,076 A | 6/1996 | Schachar | |
| 5,624,955 A | 4/1997 | Nagasawa et al. | |
| 5,665,770 A | 9/1997 | Treao et al. | |
| 5,686,450 A | 11/1997 | Hellberg et al. | |
| 5,688,828 A | 11/1997 | Hellberg et al. | |
| 5,691,379 A | 11/1997 | Ulrich et al. | |
| 5,722,952 A | 3/1998 | Schachar | |
| 5,817,630 A | 10/1998 | Hofmann et al. | |
| 5,843,184 A | 12/1998 | Cionni | |
| 5,869,468 A | 2/1999 | Freeman | |
| 5,874,455 A | 2/1999 | Terao et al. | |
| 5,888,243 A | 3/1999 | Silverstrini | |
| 6,007,510 A | 12/1999 | Nigam | |
| 6,013,462 A | 1/2000 | Kauvar et al. | |
| 6,030,950 A | 2/2000 | Ohlenschlager | |
| 6,063,116 A | 5/2000 | Kelleher | |
| 6,214,044 B1 | 4/2001 | Silverstrini | |
| 6,288,106 B1 | 9/2001 | Pearson et al. | |
| 6,313,164 B1 | 11/2001 | Fujita et al. | |
| 6,339,102 B1 | 1/2002 | Meyerhoff et al. | |
| 6,387,945 B2 | 5/2002 | Packer et al. | |
| 6,472,541 B2 | 10/2002 | Tslen et al. | |
| 6,664,287 B2 | 12/2003 | Avery et al. | |
| 6,703,039 B2 | 3/2004 | Xia et al. | |
| 6,743,779 B1 | 6/2004 | Unger et al. | |
| 6,923,955 B2 | 8/2005 | Till et al. | |
| 7,164,943 B2 | 1/2007 | Roy | |
| 7,914,815 B2 | 3/2011 | Till et al. | |
| 7,935,332 B2 | 5/2011 | Till | |
| 8,147,816 B2 | 4/2012 | Till et al. | |
| 8,410,162 B2 | 4/2013 | Garner et al. | |
| 8,647,612 B2 | 2/2014 | Garner et al. | |
| 8,697,109 B2 | 4/2014 | Garner et al. | |
| 2002/0025311 A1 | 2/2002 | Till | |
| 2002/0035243 A1 | 3/2002 | Imfeld et al. | |
| 2003/0187058 A1 | 10/2003 | Hasselwander et al. | |
| 2003/0228299 A1 | 12/2003 | Droy-Lefaix et al. | |
| 2004/0044227 A1 | 3/2004 | Klatt et al. | |
| 2004/0092586 A1 | 5/2004 | Ogata et al. | |
| 2005/0101677 A1 | 5/2005 | Till | |
| 2005/0112113 A1 | 5/2005 | Till et al. | |
| 2005/0130881 A1 | 6/2005 | Shashoua et al. | |
| 2005/0137124 A1 | 6/2005 | Castillejos | |
| 2005/0171212 A1 | 8/2005 | Gierhart et al. | |
| 2005/0287201 A1 | 12/2005 | Till et al. | |
| 2006/0177430 A1 | 8/2006 | Bhushan | |
| 2006/0188492 A1 | 8/2006 | Richardson et al. | |
| 2007/0055070 A1 | 3/2007 | Lawrence | |
| 2007/0207116 A1 | 9/2007 | Brown | |
| 2007/0293562 A1 | 12/2007 | Mylari et al. | |
| 2008/0038316 A1 | 2/2008 | Wong et al. | |
| 2008/0139990 A1 | 6/2008 | Till et al. | |
| 2008/0213239 A1 | 9/2008 | Morris | |
| 2009/0082281 A1 | 3/2009 | Shashoua | |
| 2009/0093541 A1 | 4/2009 | Ogata | |
| 2009/0192212 A1 | 7/2009 | Garner et al. | |
| 2009/0227677 A1 | 9/2009 | Garner et al. | |
| 2010/0098653 A1 | 4/2010 | Yu et al. | |
| 2010/0317608 A1 | 12/2010 | Garner et al. | |
| 2011/0135622 A1 | 6/2011 | Till et al. | |
| 2014/0121266 A1 | 5/2014 | Garner et al. | |

FOREIGN PATENT DOCUMENTS

| | | |
|---|---|---|
| WO | WO 93/25199 | 12/1993 |
| WO | WO 94/01773 | 1/1994 |
| WO | WO 02/13863 | 2/2002 |
| WO | WO 02/056804 | 7/2002 |
| WO | WO 03/084532 | 10/2003 |
| WO | WO 2004/028536 | 4/2004 |
| WO | WO 2005/084635 | 9/2005 |
| WO | WO 2006/047080 | 5/2006 |
| WO | 2007011874 * | 1/2007 |
| WO | WO 2007/011874 | 1/2007 |
| WO | WO 2008/120070 | 10/2008 |
| WO | WO 2010/054135 | 5/2010 |
| WO | WO 2010/147962 | 12/2010 |

OTHER PUBLICATIONS

Applegate, M. A., K. M. Humphries, and L. I. Szweda. Jan. 2007. Reversible Inhibition of alpha-Ketoglutarate Dehydroagenase by Hydrogen Perodixe: Glutathionylation and Protection of Lipoic Acid. Biochemistry. 47(1): 473-478.

Argirova, M., M. Kleine-Reidick, and W. Breipohl. 2004. Redox status of the eye lens: a regional study. Cell biochemistry and biophysics 41: 381-390.

Ariga T, et al. 2000. Antithrombotic and antineoplastic effects of phyto-organosulfur compounds. Biofactors. 13(1-4):251-5.

Arora A, et al. 2004. Reversal of P-glycoprotein-medicated multidrug resistance by diallyl sulfide in K562 leukemic cells and in mouse liver. Carcinogenesis. 25(6):941-9. Epub Jan. 16, 2004.

Asmellash S, et al. 2005. Modulating the endoplasmic reticulum stress response with trans-4,5-dihydroxy-1,2-dithiane prevents chemically induced renal injury in vivo. Toxicol Sci. 88(2):576-84. Epub Sep. 8, 2005.

Baghieri, S., and M. H. Garner. 1992. Na,K-ATPase and phospholipid degradation in bovine and human lenses. Current eye research 11: 459-467.

Belloir C, et al. 2006. Protective effects of garlic sulfur compounds against DNA damage induced by direct- and indirect-acting genotoxic agents in HepG2 cells. Food Chem Toxicol. 44(6):827-34.

Bilska, A., and L. Wlodek. 2005. Lipoic acid—the drug of the future? Pharmacol Rep 57: 570-577.

Bilska, A., M. Dubiel, M. Sokolowska-Jezewicz, E. Lorenc-Koci, and L. Wlodek. Jun. 2007. Alpha-lipoic acid differently affects the reserpine-induced oxidative stress in the striatum and prefrontal cortex of rat brain. Neuroscience 146: 1758-1771.

Bitar, M. S., S. Wahid, C. W. Pilcher, E. Al-Saleh, and F. Al-Mulla. 2004. Alpha-lipoic acid mitigates insulin resistance in Goto-Kakizaki rats. Hormone and metabolic research. Hormon- und Stoffwechselforschung 36: 542-549.

Blanco, R. A., T. R. Ziegler, B. A. Carlson, P. Y. Cheng, Y. Park, G. A. Cotsonis, C. J. Accardi, and D. P. Jones. Oct. 2007. Diurnal variation in glutathione and cysteine redox states in human plasma. The American journal of clinical nutrition 86: 1016-1023.

Blankenship, T. N., J. F. Hess and P. G. FitzGerald. 2001. Development- and differentiation-dependent reorganization of intermediate filaments in fiber cells. Investigative ophthalmology & visual science 42: 735-742.

Bonomi, L et al. 1990. Evaluation of the 701 interzeag lens opacity meter. Graefe's Arch Clin Exp Ophthalmol 228(5):447-9.

Borja, D et al. Jun. 2008. Optical Power of the Isolated Human Crystalline Lens. Invest Ophthalmol Vis Sci 49(6):2541-8.

Bron, A.J., et al. "The Ageing Lens" Ophthalmologica (2000) 214(1):86-104.

Brunkener, M., and S. D. Georgatos. 1992. Membrane-binding properties of filensin, a cytoskeletal protein of the lens fiber cells. Journal of cell science 103 ( Pt 3): 709-718.

Cenedella, R. J. 1998. Prenylation of proteins by the intact lens. Investigative ophthalmology & visual science 39: 1276-1280.

(56) References Cited

OTHER PUBLICATIONS

Croft, M. A., A. Glasser, G. Heatley, J. McDonald, T. Ebbert, N. V. Nadkarni, and P. L. Kaufman, 2006. The zonula, lens, and circumlental space in the normal iridectomized rhesus monkey eye. Investigative ophthalmology & visual science 47: 1087-1095.

Croft, M. A., and P. L. Kaufman. 2006. Accommodation and presbyopia: the ciliary neuromuscular view. Ophthalmology clinics of North America 19: 13-24, v.

Dubbelman, M., G. L. Van der Heijde, H. A. Weeber, and G. F. Vrensen. 2003. Changes in the internal structure of the human crystalline lens with age and accommodation. Vision research 43: 2363-2375.

Eason, R. C., H. E. Archer, S. Akhtar, and C. J. Bailey. 2002. Lipoic acid increases glucose uptake by skeletal muscles of obese-diabetic ob/ob mice. Diabetes Obes Metab 4: 29-35.

Egan, D., P. James, D. Cooke, and R. O'Kennedy. 1997. Studies on the cytostatic and cytotoxic effects and mode of action of 8-nitro-7-hydroxycoumarin. Cancer letters 118: 201-211.

Finn, G., B. Creaven, and D. Egan. 2003. Modulation of mitogen-activated protein kinases by 6-nitro-7-hydroxycoumarin mediates apoptosis in renal carcinoma cells. European journal of pharmacology 481: 159-167.

Finn, G. J., B. S. Creaven, and D. A. Egan. 2004. A study of the role of cell cycle events mediating the action of coumarin derivatives in human malignant melanoma cells. Cancer letters 214: 43-54.

Flammer J, Bebie H. 1987. Lens Opacity Meter: a new instrument to quantify lens opacity. Ophthalmologica 195(2):69-72.

Furuta, T., S. S. Wang, J. L. Dantzker, T. M. Dore, W. J. Bybee, E. M. Callaway, W. Denk, and R. Y. Tsien. 1999. Brominated 7-hydroxycoumarin-4-ylmethyls: photolabile protecting groups with biologically useful cross-sections for two photon photolysis. Proceedings of the National Academy of Sciences of the United States of America 96: 193-1200.

Gail MH & You WC. 2006. A factorial trial including garlic supplements assesses effect in reducing precancerous gastric lesions. J Nutr. 136(3 Suppl):813S-815S.

Garner, M. H., and J. Horwitz. 1994. Catalytic subunit isoforms of mammalian lens Na,K-ATPase. Current eye research 13: 65-77.

Garner, M. H., and Y. Kong. 1999. Lens epithelium and fiber Na,K-ATPases: distribution and localization by immunocytochemistry. Investigative ophthalmology & visual science 40: 2291-2298.

Garner, M. H., and J. R. Kuszak. 1993. Cations, oxidants, lights as causative agents in senile cataracts. Puerto Rico health sciences journal 12: 115-122.

Garner, M. H., and A. Spector. 1980. Selective oxidation of cysteine and methionine in normal and senile cataractous lenses. Proceedings of the National Academy of Sciences of the United States of America 77: 1274-1277.

Garner, M. H. 1994. Na,K-ATPases of the lens epithelium and fibe cell: formation of catalytic cycle intermediates and Na+: K+ exchange. Experimental eye research 58: 705-718.

Gilmore WJ & Kirby GM. 2004. Endoplasmic reticulum stress due to altered cellular redox status positively regulates murine hepatic CYP2A5 expression. J. Pharmacol Exp Ther. 308(2):600-8. Epub Nov. 10, 2003.

Glasser, A., and M. C. Campbell. 1999. Biometric, optical and physical changes in the isolated human crystalline lens with age in relation to presbyopia. Vison research 39: 1991-2015.

Goulielmos, G., F. Gounari, S. Remington, S. Muller, M. Haner, U. Aebi, and S. D. Georgatos. 1996. Filensin and phakinin form a novel type of beaded intermediate filaments and coassemble de novo in cultured cells. The Journal of cell biology 132: 643-655.

Goulielmos, G., S. Remington, F. Schwesinger, S. D. Georgatos, and F. Gounari. 1996. Contributions of the structural domains of filensin in polymer formation and filament distribution. Journal of cell science 109 ( Pt 2): 447-456.

Green DR & Reed JC. 1998. Mitochondria and apoptosis. Science 281(5381):1309-12.

Gruzman, A., A. Hidmi, J. Katzhendler, A. Haj-Yehie, and S. Sasson. 2004. Synthesis and characterization of new and potent alpha-lipoic acid derivatives. Bioorganic & medicinal chemistry 12: 1183-1190.

Guest, P. C., H. A. Skynner, K. Salim, F. D. Tattersall, M. R. Knowles, and J. R. Atack. 2006. Detection of gender differences in rat lens proteins using 2-D-DIGE. Proteomics 6: 667-676.

Gurney, AM. 1994. Flash photolysis of caged compounds in Microelectrode Techniques, ed Ogden D, pp. 389-406.

Halhal M, et al. 2004. Iontophoresis: from the lab to the bed side. Exp Eye Res 78(3):751-57.

Halleck MM, et al. 1997. Reduction of trans-4,5-dihydroxy-1,2-dithiane by cellular oxidoreductases activates gadd153/chop and grp78 transcription and induces cellular tolerance in kidney epithelial cells. J Biol Chem. 272(35):21760-6.

Heidemann, S. R., S. Kaech, R. E. Buxbaum, and A. Matus. 1999. Direct observations of the mechanical behaviors of the cytoskeleton in living fibroblasts. The Journal of cell biology 145: 109-122.

Hardie, R.C. 1995. Photolysis of Caged Ca2+ Facilitates and inactivates but Does Not Directly Excite Light-Sensitive Channels in Drosophila Photoreceptors. The Journal of Neuroscience 15(1):899-902.

Hermans, E., M. Dubbelman, R. van der Heijde, and R. Heethaar. Jul. 2007. The shape of the human lens nucleus with accommodation. Journal of vision 7: 16.1-10.

Hoenders, H.J., et al. "Lens proteins and aging" J Gerontol (May 1983) 38(3):278-86.

Hofmann, M., P. Mainka, H. Tritschler, J. Fuchs, and G. Zimmer. 1995. Decrease of red cell membrane fluidity and -SH groups due to hyperglycemic conditions is counteracted by alpha-lipoic acid. Archives of biochemistry and biophysics 324: 85-92.

Hung CC, et al. 2003. Protection of renal epithelial cells against oxidative injury by endoplasmic reticulum stress preconditioning is mediated by ERK1/2 activation. J Biol Chem. 278(31):29317-26. Epub May 8, 2003.

Ivanov, D., G. Dvoriantchikova, A. Pestova, L. Nathanson, and V. I. Shestopalov. 2005. Microarray analysis of fiber cell maturation in the lens. FEBS letters 579: 1213-1219.

Janoria, K. G., S. Hariharan, D. Paturi, D. Pal, and A. K. Mitra. 2006. Biotin uptake by rabbit corneal epithelial cells: role of sodium-dependent multivitamin transporter (SMVT). Current eye research 31: 797-809.

Jimenez-Orozco, F. A., J. S. Lopez-Gonzalez, A. Nieto-Rodriguez, M. A. Velasco-Velazquez, J. A. Molina-Guarneros, N. Mendoza-Patino, M. J. Garcia-Mondragon, P. Elizalde-Galvan, F. Leon-Cedeno, and J. J. Mandoki. 2001. Decrease of cyclin D1 in the human lung adenocarcinoma cell line A-427 by 7-hydroxycoumarin. Lung cancer (Amsterdam, Netherlands) 34: 185-194.

Johansson, M., and M. Lundberg. Dec. 2007. Glutathionylation of beta-actin via a cysteinyl sulfenic acid intermediary. BMC Biochem 8: 26.

Jones, D. P., Y. M. Go, C. L. Anderson, T. R. Ziegler, J. M. Kinkade, Jr., and W. G. Kirlin. 2004. Cysteine/cystine couple in a newly recognized node in the circuitry for biologic redox signaling and control. Faseb J 18: 1246-1248.

Jung MY, et al. 2001. Chemopreventive allylthiopyridazine derivatives induce apoptosis in SK-Hep-1 hepatocarcinoma cells through a caspase-3-dependent mechanism. Eur J Cancer. 37(16):2104-10.

Jürgen, W. Mar. 2007. Synthesis and investigations of (6-hydroxy-3-oxo-3H-xanthen-9-yl)methyl derivatives. A new photoremovable protecting group. Inaugural Disseration of Universität Basel.

Kahn, J., P. Preis, F. Waldman, and A. Tseng, Jr. 1994. Coumarin modulates the cell-cycle progression of an MTV-EJras cell line. Journal of cancer research and clinical oncology 120 Suppl: S19-22.

Kao, J.P.Y. 2006. Caged Molecules: Principles and Practical Considerations. Current Protocols in Neuroscience. 6.20.1-6.20.21.

Kibbelaar, M. A., F. C. Ramaekers, P. J. Ringens, A. M. Selten-Versteegen, L. G. Poels, P. H. Jap, A. L. van Rossum, T. E. Feltkamp, and H. Bloemendal. 1980. Is actin in eye lens a possible factor in visual accomodations? Nature 285: 506-508.

Kim DH, et al. 2005. Aqueous penetration and biological activity of moxifloxacin 0.5% ophthalmic solution and gatifloxacin 0.3% solution in cataract surgery patients. Ophthalmology 112(11):1992-6. Epub Sep. 23, 2005.

(56) References Cited

OTHER PUBLICATIONS

Konrad, D., R. Somwar, G. Sweeney, K. Yaworsky, M. Hayashi, T. Ramlal, and A. Klip. 2001. The antihyperglycemic drug alpha-lipoic acid stimulates glucose uptake via both GLUT4 translocation of GLUT4 activation: potential role of p38 mitogen-activated protein kinase in GLUT4 activation. Diabetes 50: 1464-1471.

Krueger, R.R., et al. "Experimental increase in accommodative potential after neodymium: yttrium-aluminum-garnet laser photodisruption of paired cadaver lenses" Ophthalmology (2001) 108(11):2122-29.

Krumdieck, C.L., et al. "Mechanism of Homocysteine Toxicity on Connective Tissues: Implications for the Morbidity of Aging" J. Nutr. (2000) 130:365S-68S.

Kumar RV, et al. 1991. The Nature of inhibition of 3-hydroxy-3-methylglutaryl CoA reductase by garlic-derived diallyl disulfide. Biochim Biophys Acta. 1078(2):219-25.

Kuszak, J. R., A. R. Khan, and R. J. Cenedella. 1988. An ultrastructural analysis of plasma membrane in the U18666A cataract. Investigative ophthalmology & visual science 29: 261-267.

Lacy, A., and R. O'Kennedy. 2004. Studies on coumarins and coumarin-related compounds to determine their therapeutic role in the treatment of cancer. Current pharmaceutical design 10: 3797-3811.

Larsson, H. P., A. V. Tzingounis, H. P. Koch, and M. P. Kavanaugh. 2004. Fluorometric measurements of conformational changes in glutamate transporters. Proceedings of the National Academy of Sciences of the United States of America 101: 3951-3956.

Lee V & Bundgaard H. 1992. Improved Ocular Drug Delivery with Prodrugs. In: Sloan K. ed. Prodrugs: Topical and Ocular Drug Delivery, vol. 53, p. 233.

Lesiński L. & Duschmalé J. 2006. Flash Photolysis in Praktikum "Physikalische Chemie" pp. 1-8.

Li, L., J. Lim, M. D. Jacobs, J. Kistler, and P. J. Donaldson. Mar. 2007. Regional differences in cystine accumulaton point to a sutural delivery pathway to the lens core. Investigative opthalmology & visual science 48: 1253-1260.

Lim, J., Y. C. Lam, J. Kistler, and P. J. Donaldson. 2005. Molecular characterization of the cystine/glutamate exchanger and the excitatory amino acid transporters in the rat lens. Investigative ophthalmology & visual science 46: 2869-2877.

Lim, J., L. Li, M. D. Jacobs, J. Kistler, and P. J. Donaldson. Nov. 2007. Mapping of glutathione and its precursor amino acids reveals a role for GLYT2 in glycine uptake in the lens core. Investigative ophthalmology & visual science 48: 5142-5151.

Lindsey Rose, K. M., R. G. Gourdie, A. R. Prescott, R. A. Quinlan, R. K. Crouch, and K. L. Schey. 2006. The C terminus on lens aquaporin 0 interacts with the cytoskeletal proteins filensin and CP49. Investigative ophthalmology & visual science 47: 1562-1570.

Liu H, et al. 1997. Endoplasmic reticulum chaperones GRP78 and calreticulin prevent oxidative stress, Ca2+ distrubances, and cell death in renal epithelial cells. J Biol Chem. 272(35):21751-9.

Liu, J., E. Head, A. M. Gharib, W. Yuan, R. T. Ingersoll, T. M. Hagen, C. W. Cotman, and B. N. Ames. 2002. Memory loss in old rats is associated with brain mitochondrial decay and RNA/DNA oxidation: partial reversal by feeding acetyl-L-carnitine and/or R-alpha-lipoic acid. Proceedings of the National Academy of Sciences of the United States of America 99: 2356-2361.

Lopez-Gonzalez, J. S., H. Padro-Garcia, D. Aguilar-Cazares, J. A. Molina-Guarneros, J. Morales-Fuentes, and J. J. Mandoki. 2004. Apoptosis and cell cycle disturbances induced by coumarin and 7-hydroxycoumarin on human lung carcinoma cell lines. Lung cancer (Amsterdam, Netherlands) 43: 275-283.

Luo, S., V. S. Kansara, X. Zhu, N. K. Mandava, D. Pal, and A. K. Mitra. 2006. Functional characterization of sodium-dependent multivitamin transporter in MDCK-MDR1 cells and its utilization as a target for drug delivery. Mol Pharm 3: 329-339.

Maitra, I., E. Serbinova, H. J. Tritschler, and L. Packer, 1996. Stereospecific effects of R-lipoic acid on buthionine sulfoximine-induced cataract formation in newborn rats. Biochemical and biophysical research communications 221: 422-429.

Maitra, I., E. Serbinova, H. Trischler, and L. Packer. 1995. Alpha-lipoic acid prevents buthionine sulfoximine-induced cataract formation in newborn rats. Free radical biology & medicine 18: 823-829.

Manns, F., J. M. Parel, D. Denham, C. Billotte, N. Ziebarth, D. Borja, V. Fernandez, M. Aly, E. Arrieta, A. Ho, and B. Holden. Jul. 2007. Optomechanical response of human and monkey lenses in a lens stretcher. Investigative ophthalmology & visual science 48: 3260-3268.

Merdes, A., M. Brunkener, H. Horstmann, and S. D. Georgatos. 1991. Filensin: a new vimentin-binding, polymerization-competent, and membrane-associated protein of the lens fiber cell. The Journal of cell biology 115: 397-410.

Merdes, A., F. Gounari, and S. D. Georgatos, 1993. The 47-kD lens-specific protein phakinin is a tailless intermediate filament protein and an assembly partner of filensin. The Journal of cell biology 123: 1507-1516.

Moffat, B.A., et al. "Age-related Changes in the Kinetics of Water Transport in Normal Human Lenses" Exp. Eye Res. (1999) 69(6):663-69.

Moini, H., O. Tirosh, Y. C. Park, K. J. Cho, and L. Packer. 2002. R-alpha-lipoic acid action on cell redox status, the insulin receptor, and glucose uptake in 3T3-L1 adipocytes. Archives of biochemistry and biophyics 397: 384-391.

Muchowski, P. J., M. M. Valdez, and J. I. Clark. 1999. AlphaB-crystallin selectively targets intermediate filament proteins during thermal stress. Investigative ophthalmology & visual science 40: 951-958.

Muck SR, et al. 1997. Cytotoxicity and genotoxicity of diallyl sulfide and diallyl disulfide towards Chinese hamster ovary cells. Food Chem Toxicol. 35(3-4):379-85.

Newell. 1996. Ophthalmology: Principles and Concepts St. Louis: Mosby-Year Book St. Louis, p. 83.

Obrosova I, et al. 1998. Diabetes-induced changes in lens antioxidant status, glucose utilization and energy metabolism: effect of DL-alpha-lipoic acid. Diabetologia 41(12):1442-50.

Ong, M. D., D. M. Payne, and M. H. Garner. 2003. Differential protein expression in lens epithelial whole-mounts and lens epithelial cell cultures. Experimental eye research 77: 35-49.

Pau, H., and J. Kranz. 1991. The increasing sclerosis of the human lens with age and its relevance to accommodation and presbyophia. Graefe's archive for clinical and experimental ophthalmology—Albrecht von Graefes Archiv fur klinische und experimentelle Ophthalmologie 229: 294-296.

Petit PX, et al. 1995. Alterations in mitochondrial structure and function are early events of dexamethasone-induced thymocyte apoptosis. J Cell Biol. 130(1):157-67.

Phelps-Brown, N.A., et al. "Nutritional supplements and the eye" Eye (1998) 12:127-33.

Pierscionek, B. K. 1995. Age-related response of human lenses to stretching forces. Experimental eye research 60: 325-332.

Reddy, N. S., K. Gumireddy, M. R. Mallireddigari, S. C. Cosenza, P. Venkatapuram, S. C. Bell, E. P. Reddy, and M. V. Reddy. 2005. Novel coumarin-3-(N-aryl)carboxamides arrest breast cancer cell growth by inhibiting ErbB-2 and ERK1. Bioorganic & medicinal chemistry 13: 3141-3147.

Salvioli S, et al. 1997. JC-1, but not DiOC6(3) or rhodamine 123, is a reliable fluorescent probe to assess delta psi changes in intact cells: implications for studies on mitochondrial functionality during apoptosis. FEBS Lett. 411(1):77-82.

Sandilands, A., A. R. Prescott, A. M. Hutcheson, R. A. Quinlan, J. T. Casselman, and P. G. FitzGerald. 1995. Filensin is proteolytically processed during lens fiber cell differentiation by multiple independent pathways. European journal of cell biology 67: 238-253.

Sarraf D & Lee DA. 1994. The Role of Iontophoresis in Ocular Drug Delivery. J. Ocul Pharmacol 10(1):69-81.

Sato, H., J. Tamba, K. Kuriyama-Matsumura, S. Okuno, and S. Bannai. 2000. Molecular cloning and expression of human xCT, the light chain of amino acid transport system xc. Antioxid Redox Signal 2: 665-671.

Sato, H., M. Tamba, T Ishii, and S. Bannai. 1999 Cloning and expression of a plasma membrane cystine/glutamate exchange transporter composed of two distinct proteins. The Journal of biological chemistry 274: 11455-11458.

(56) References Cited

OTHER PUBLICATIONS

Sato, H., A. Shiiya, M. Kimata, K. Maebara, M. Tamba, Y. Sakakura, N. Makino, F. Sugiyama, K. Yagami, T. Moriguchi, S. Takahashi, and S. Bannai. 2005. Redox imbalance in cystine/glutamate transporter-deficient mice. The Journal of biological chemistry 280: 37423-37429.

Schonheit, K., L. Gille, and H. Nohl. 1995. Effect of alpha-lipoic acid and dihydrolipoic acid on ischemia/reperfusion injury of the heart and heart mitochondria. Biochimica et biophysica acta 1271: 335-342.

Senda, N. 2006. Synthesis and Photochemical Properties of a New Water-Soluble Coumarin, Designed as a Chromophore for Highly Water-Soluble and Photolabile Protecting Group. Bull. Chem. Soc. Jpn. vol. 79, No. 11, 1753-1757.

Shembekar, V. R., Y. Chen, B. K. Carpenter, and G. P. Hess. 2005. A protecting group for carboxylic acids that can be photolyzed by visible light. Biochemistry 44: 7107-7114.

Spector, A., et al. "Thioredoxin fragment 31-36 is reduced by dihydrolipoamide and reduces oxidized protein" Biochem Biophys Res Commun (Jan. 1988) 150(1):156-62.

Strenk, S. A., L. M. Strenk, J. L. Semmlow, and J. K. DeMarco. 2004. Magnetic resonance imaging study of the effects of age and accommodation on the human lens cross-sectional area. Investigative ophthalmology & visual science 45: 539-545.

Sundaram SG & Milner JA. 1996. Diallyl disulfide suppresses the growth of human colon tumor cell xenografts in athymic nude mice. J Nutr. 126(5):1355-61.

Sweeney, M. H., and R. J. Truscott. 1998. An impediment to glutathione diffusion in older normal human lenses: a possible precondition for nuclear cataract. Experimental eye research 67: 587-595.

Tamm, E., E. Lutjen-Drecoll, W. Jungkunz, and J. W. Rohen. 1991. Posterior attachment of ciliary muscle in young, accommodating old, presbyopic monkeys. Investigative ophthalmology & visual science 32: 1678-1692.

Tamm, S., E. Tamm, and J. W. Rohen. 1992. Age-related changes of the human ciliary muscle. A quantitative morphometric study. Mechanisms of ageing and development 62: 209-221.

Truscott, R. J. 2000. Age-related nuclear cataract: a lens transport problem. Ophthalmic research 32: 185-194.

Wang, C. J., Y. J. Hsieh, C. Y. Chu, Y. L. Lin, and T. H. Tseng. 2002. Inhibition of cell cycle progression in human leukemia HL-60 cells by esculetin. Cancer letters 183: 163-168.

Wang, S. J., and H. H. Chen. Jan. 2007. Presynaptic mechanisms underlying the alpha-lipoic acid facilitation of glutamate exocytosis in rat cerebral cortex nerve terminals. Neurochemistry international 50: 51-60.

Weeber, HA et al. Feb. 2007. Stiffness gradient in the crystalline lens. Graefes Arch Clin Exp Ophthalmol 245(9):1357-66.

Widomska, J., M. Raguz, J. Dillon, E. R. Gaillard, and W. K. Subczynski. Jun. 2007. Physical properties of the lipid bilayer membrane made of calf lens lipids: EPR spin labeling studies. Biochimica et biophysica acta 1768: 1454-1465.

Wieboldt, R. et al. 1994. Photolabile precursors of glutamate: Synthesis, photochemical properties, and activation of glutamate receptors on a microsecond time scale. Proc. Natl. Acad. Sci, 91:8752-8756.

Willner I & Zahavy E. 1994. Activation of Glutathione Reducase by Light: A Novel Approach to Design Redox Photo-Enzymes. Angew Chem Int Ed Engl 33(5):5281-83.

Yin MC, et al. 2002. Nonenzymatic antioxidant activity of four organosulfur compounds derived from garlic. J Agric Food Chem. 50(21):6143-7.

Yu, N. T., D. C. DeNagel, P. L. Pruett, and J. F. Kuck, Jr. 1985. Disulfide bond formation in the eye lens. Proceedings of the National Academy of Sciences of the United States of America 82: 7965-7968.

Zhao, Y., Q. Zheng, K. Dakin, K. Xu, M. L. Martinez, amd W. H. Li. 2004. New caged coumarin fluorophores with extraordinary uncaging cross sections suitable for biological imaging applications. Journal of the American Chemical Society 126: 4653-4663.

Zivkovic, D. Apr. 2007. Investigations on 2,7-diamino-9-fluorenol photochemistry. Inaugural Dissertation at Universität Basel.

Ip C, Ganther HE. 1992. Comparison of selenium and sulfer analogs in cancer prevention. Carcinogenesis. 13(7): 1167-70.

Bustamante, J., et al., 1998. α-Lipoic Acid in Liver Metabolism and Disease. Free Radical Biology & Medicine 24: No. 6 1023--1039.

Cagini, C. MD, et al. 2010. Study of alpha-lipoic acid penetration in the human aqueous humour after topical administration. Clinical and Experimental Ophthalmology "Accepted Article" doi: 10.1111/j.1442-9071.2010.02319.x.

Giblin FJ, et al. 1979. The effects of X-irradiation on lens reducing systems. Investigative Ophthalmology & Visual Science 18:468-475.

Kramár P, et al. 1987. Thermal cataract formation in rabbits. NCBI Pubmed abstract, PMID: 3426637, abstract of Bioelectromagnetics 8:397-406.

Li, X., Liu, Z., et al. Apr. 2008. Lipoamide protects retinal pigment epithelial cells from oxidative stress and mitochondrial dysfunction. Free Radic Biol Med. 44(7): 1465-1474.

Lipman RM, et al. 1988. Cataracts induced by Microwave and Ionizing Radiation. NCBI Pubmed abstract, PMID: 3068822, abstract of Surv. Ophthalmol 33:200-210.

Trayhurt P. and Van Heyningen R. 1973. The Metabolism of Amino Acids in the Bovine Lens; Their Oxidation as a Source of Energy. Biochem. J. 136:67-75.

Wakabayashi, Y. et al. 2006. Glutamate Levels in Aqueous Humor of Patients with Retinal Artery Occlusion. Retina 26:432-436.

Zwingmann, C. et al. 2001. 13C Isotopomer Analysis of Glucose and Alanine Metabolism Reveals Cytosolic Pyruvate Compartmentation as Part of Energy Metabolism in Astrocytes. GLIA 34:200-212.

Aloisi et al. 1948. Glycerylphosphorylcholine and Choline Glycerophosphate. Biochemical Journal. vol. 43, pp. 157-161; p. 157; col. 1, para 2-3; col. 2, para 1; p. 158, col. 1, para 4.

Gilbert, Basic Concepts in Biochemistry USA. McGraw Hill 2000 p. 184.

Jablonski et al. Plant Physiology 1978 61:221-225.

Ng et al. Experimental Eye Research 1986 43:477-489.

Morris Jr. Recent advances in arginine metabolism; roles and regulation of the arginases. British Journal of Pharmacology, E-Pub Jun. 5, 2009, 157(6):922-930.

PubChem Compound Summary CID 863 lipoamide (Sep. 16, 2004) (Retrieved from the internet Nov. 13, 2010; http://pubchem.ncbi.nlm.nih.gov/summary/summary.cgi?cid=863.

Salceda, et al. L-arginine uptake in normal and diabetic rat retina and retinal pigment epithelium. Neurochem Res., Aug. 2008, 33(8):1541-1545.

Stuehr et al. Nw-Hydroxy-L-arginine is an intermediate in the Biosynthesis of nitric Oxide from L-Arginine. The Journal of Biological Chemistry 1991, 266(10):6259-6263.

Truscott. Presbyopia. Emerging from a blur towards an understanding of the molecular basis for this most common eye condition. Exp Eye Res., Epub Jul. 2008, 88(2):241-247; p. 241, col. 1; p. 242, col. 1; p. 245, col. 1.

English Translation of Office Action mailed Jun. 21, 2011, in Japanese Patent Application No. JP 2007-537922 A, filed Dec. 27, 2007.

Extended European Search Report mailed on Apr. 19, 2012, for EP Application No. 09825411.0, European Patent Office, Germany.

Office Action received in U.S. Appl. No. 12/815,586 dated May 9, 2012.

Extended European Search Report mailed on Aug. 21, 2012, for EP Application No. 10790038.3, European Patent Office, Netherlands.

English Translation of Office Action mailed Oct. 12, 2012, in Mexican Patent Application No. MX/a/2007/004775.

* cited by examiner

Glutathione

Cystine

DITHIOL COMPOUNDS AND TREATMENT OF PRESBYOPIA USING SAID COMPOUNDS

CROSS-REFERENCES TO RELATED APPLICATIONS

This application is a continuation of U.S. application Ser. No. 12/390,928, filed Feb. 23, 2009, now U.S. Pat. No. 8,647,612, which claims the benefit of U.S. Appl. No. 61/033,870 filed Mar. 5, 2008, U.S. Appl. No. 61/060,487 filed Jun. 11, 2008, and U.S. Appl. No. 61/077,186 filed Jul. 1, 2008. This application is also a continuation-in-part of U.S. application Ser. No. 12/267,260 filed Nov. 7, 2008, now U.S. Pat. No. 8,697,109. Each of these applications is incorporated herein by reference in its entirety.

BACKGROUND OF THE INVENTION

As we age, our lenses undergo physiological changes that make it more difficult to focus on near objects. That is why nearly everyone requires reading glasses, even as early as age 35-40. The ability of the eye to change focal power, also known as accommodative amplitude, decreases significantly with age. The accommodative amplitude is 20 diopters in children and young adults, but it decreases to 10 diopters by age 25 and to ≤1 diopter by age 60. The age-related inability to focus on near objects is called presbyopia. All of us will develop presbyopia and will require corrective lenses unless a new treatment is found.

In a healthy eye, the ciliary muscle can deform the lens via the suspensory ligaments to change the focal power of the eye. The lens takes on a different shape when the ciliary muscle is relaxed for near vision (FIG. 2A) than when the ciliary muscle is contracted for far vision (FIG. 2B). When the ciliary muscle is relaxed, the central thickness is larger, and the equatorial circumference is smaller. Also, the lens nucleus is more posterior than central, and the space between iris and lens is larger. These changes involve the fibers of the lens cortex (C) because even by young adulthood, the lens nucleus (N) is incompressible.

The ciliary muscle, the suspensory ligaments, the posterior chamber of the aqueous humor, and the lens all must be considered when defining the etiology of presbyopia. Presbyopia may be caused, in part, by lens growth, oxidative stress, and disulfide bond formation.

The lens is a unique stratified epithelium where new fiber cells are laid down in shells throughout life. But the older fibers are not sloughed, so cross-sectional area, equatorial circumference, total volume, and weight increase all with age. The anterior part of each fiber cell must differ from that of the posterior because the anterior cortex is thicker than the posterior. Furthermore, elasticity decreases in the anterior cortex with age. Because of the change in lens size, the amount of force required to change its shape increases. The circumlental space decreases causing the posterior aqueous volume to decrease. This phenomenon is more pronounced in the temporal quadrant. There are also aging changes in the ciliary muscle and suspensory ligaments that contribute to the loss of lens deformability.

Although growth is a major contributor to the decreased deformability in the presbyopic lens, small changes in fiber membrane and/or cytoskeleton structure also play a role. Lens fiber plasma membranes are relatively stable and immobile due to the high levels of sphingomyelin and cholesterol that ranges from 50 percent in the cortex to 90 percent in the nucleus. While targeting lens membrane lipids may improve deformability, it may increase the risk for cataract because cataract is associated with decreased cholesterol.

The cytoskeleton is equally critical for fiber stability and elasticity. The lens fiber has actin microfilaments, a unique beaded intermediate filament, and microtubules, all of which are associated with the inner leaflet of the fiber plasma membrane. Disulfide bonds in intrinsic membranes and in membrane associated proteins increase with age in the non-cataractous human lens and in rodent lenses. Glutathione, believed to be the lens' major defense against oxidation, decreases with age and with distance from the lens surface. In other systems, glutathionylation of actin causes actin-microfilament depolymerization. Actin microfilaments are the most elastic of the cytoskeletal components.

Such disulfide bonds can also induce cataract. Oxidative stress can oxidize lens proteins, which destroys the balanced redox state required to maintain transparency. Thiolation of lens protein changes the tertiary structure of the protein, and more functional groups are exposed for further modification. The first line of defense, endogenously high levels of glutathione, fends off reactive oxygen species and keep lens proteins in a reduced state. As a second line of defense, intrinsic repair enzymes dethiolate the protein-thiol mixed disulfides or protein-protein disulfides induced by oxidative stress, thus keeping lens proteins thiols free and restoring lens proteins-enzyme function and activity.

With age, these protection and repair mechanisms against oxidative stress slowly deteriorate and become ineffective, resulting in a lens less able to counteract the effects of reactive oxygen species and other oxidants. Sulfhydrals are among groups most susceptible to oxidation. Sulfhydral groups may then undergo oxidation creating intra- and inter-molecular cross-links which increases with age in normal human lenses. These disulfide cross-links are present in water insoluble protein fractions. High molecular weight aggregates containing proteins and membrane particles with sizes over $5 \times 10^7$ Da will scatter light. When a sufficient number of high molecular weight protein aggregates of this size or greater occur, transparency is lost and cataract occurs. Thus disulfide bond formation may be a cause of both presbyopia and cataract.

Both presbyopia and cataract are age-related and may share common etiologies such as lens growth, oxidative stress, and/or disulfide bond formation.

There is a need for agents, compounds, compositions, and methods for combating ocular disease, including presbyopia and/or cataract. The agents, compounds, compositions, and methods described herein can be prophylactic and/or therapeutic for presbyopia and cataract by preventing or reducing disulfide bond formation in lens membranes and membrane associated proteins. The agents, compounds, compositions, and methods may also affect one or more of lens growth, lens cystine and lipoic acid concentrations, cellular and lens fiber redox state, cellular elasticity, and lens transparency.

BRIEF SUMMARY OF THE INVENTION

In one embodiment, a method of treating presbyopia comprises administering an agent including at least two components independently selected from a sulfur atom, a selenium atom, and a sulfonic group. In one embodiment, at least one of the two components is selenium. The agent can be a five- or six-membered heterocycle or a non-cyclical compound.

In another embodiment, the agent has a formula of 6-A, 6-B, 6-C, 6-D, or 6-E. In another embodiment, the agent has the formula 6-A. In another embodiment, the agent has a formula 6-D or 5-E. In another embodiment, the agent has a formula 6-NC or 5-NC. In yet another embodiment, the agent has a formula 5-A or 5-B. In another embodiment, the agent has the formula NC.

Each of X and Y can be sulfur, selenium, or a sulfonic group. In one embodiment, X and Y are both sulfur. In another embodiment, one of X and Y is sulfur, and the other is sulfur or selenium.

Each R group is independently selected from the group consisting of: —H, —OH, —OAc, —OR, —SR, —$CO_2R$, an electron withdrawing group, and a linear or branched $C_{1-18}$ alkane or alkene optionally substituted by one or more substituents selected from the group consisting of ether, ester, carboxylic acid, phosphate, amide, and amine groups. In another embodiment, at least one R group is —OH or —OAc.

In yet another embodiment, at least one R group is a $C_{2-10}$ alkane or $C_{10-18}$ alkene. In another embodiment, at least one R group is —$(CH_2)_{2-10}NH_2$. In another embodiment, at least one R group is —$(CH_2)_{2-10}CO_2H$.

In one embodiment, the agent is one of the following or a derivative thereof: lipoic acid; cystine; 3,6-dihydro-1,2-dithiine; 3,4-dihydro-1,2-dithiine; 3-vinyl-[4H]-1,2-dithiine; diallyl disulfide; diallyl trisulfide; 3-prop-2-enylsulfinylsulfanylprop-1-ene; 1,2-dithiane; 6-((4R,5R)-4,5-dihydroxy-1,2-dithian-4-yl)hexanoate; (4R,5R)-5-hydroxy-1,2-dithian-4-yl acetate; (4R,5R)-1,2-dithian-4,5-diyl diacetate; or trans-4,5-dihydroxy-1,2-dithiane; or dithiothreitol.

In another embodiment, the agents are employed for pharmaceutical formulations and/or methods of treating ocular disease, e.g., presbyopia or cataract.

In one embodiment, a compound is provided that comprises an active agent X removably linked to at least one cage. The active agent can be lipoic acid or a derivative thereof. Specific exemplary active agents include 5-(1,2-dithiolan-3-yl)pentanoic acid; 5-(1,2-thiaselenolan-5-yl)pentanoic acid; 5-(1,2-thiaselenolan-3-yl)pentanoic acid; 6,8-dimercaptooctanoic acid; dihydrolipoate; 3,3'-disulanedylbis(2-aminopropanoic acid); 2-amino-3-mercaptopropanoic acid; 2-amino-3-hydroselenopropanoic acid; and salts and esters thereof.

The at least one cage can be, for example, a coumarin cage. In one embodiment, the cage is a 7-hydroxy-coumarin-4-ylmethyl-carboxyl group or a 6-bromo-7-hydroxy-coumarin-4-ylmethyl-carboxyl group. The at least one cage can be removably linked to at least one of a carboxylate group, an amino group (e.g., via —$CO_2$), or a sulfur atom of the active agent.

In another embodiment, a pharmaceutical composition for ocular use comprises a compound as described above and a pharmaceutically acceptable carrier. In another embodiment, the pharmaceutical composition for ocular use comprises cystine or seleno-cystine, or a salt or ester thereof, optionally caged by a photolabile protecting group, and a pharmaceutically acceptable carrier. The pharmaceutical compositions can include, e.g., an emulsifier and a buffered carrier.

In another embodiment, a method comprises providing or administering a caged compound and uncaging the active agent, e.g., by applying light. A chemical energy source such as glucose of NADPH can optionally be additionally provided with the caged compound.

In one embodiment, the light is UVA light and has a wavelength of about 350 to 380 nm. The light can be applied to a localized region if desired.

The method can include administration to cells in vitro or in vivo and in either case, ocular cells. The compound can be administered via a topical ocular, subtenons, subconjunctival, intracameral, intravitreal, or iontophoresis route.

The method can be used to increase or maintain accommodative amplitude, as measured in diopters, to at least 2% greater than the accommodative amplitude expected in an untreated lens of about the same age. The method can increases accommodative amplitude by at least 0.25 diopters.

The method can be used to increase or maintain lens elasticity, as measured in diopters or by elasticity E, to at least 2% greater than the elasticity expected in an untreated lens of about the same age. The method can be used to decrease or maintain lens opacity to at least 2% less than the opacity expected in an untreated lens of about the same age.

DETAILED DESCRIPTION OF THE INVENTION

Figure 1:
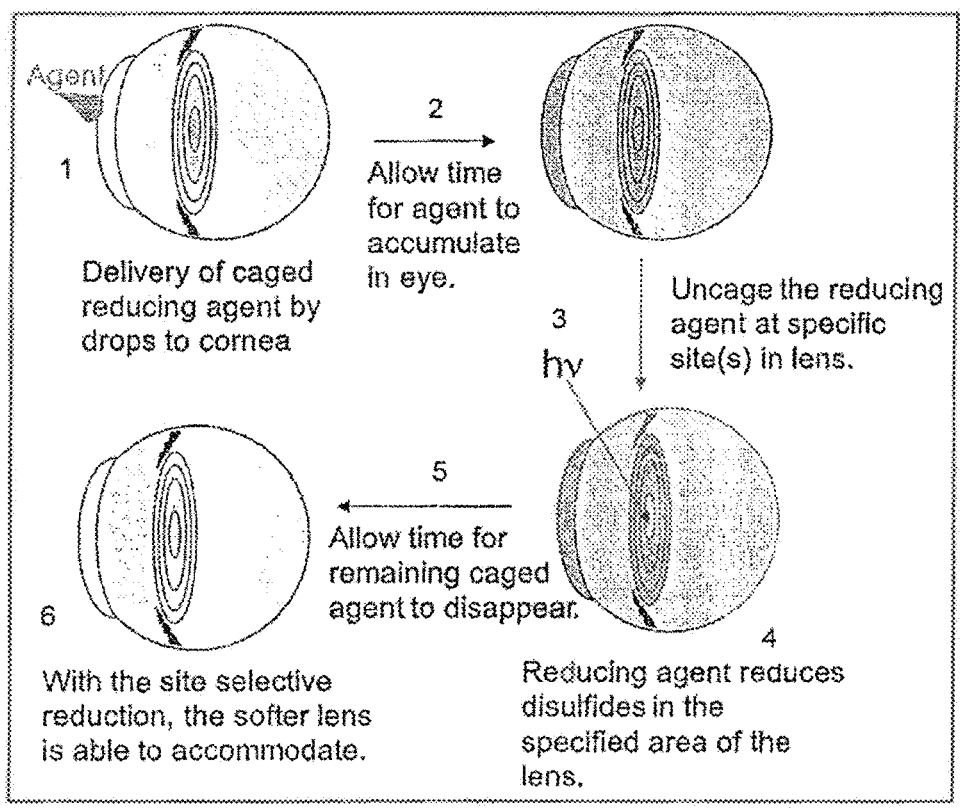
FIG. 1 is a pictorial step-wise depiction of an exemplary method as described herein. Step 1 represents delivery of a caged reducing agent by drops to the cornea. Step 2 represents allowing time to the agent to accumulate in the eye. Step 3 represents uncaging the agent at specific site(s) in the lens. Step 4 represents the agent reducing disulfide bonds in the specified site(s) in the lens. Step 5 represents allowing time for the remaining caged compound to disappear. Step 6 represents a softer lens that is better able to accommodate after site selective reduction.
Figure 2A:
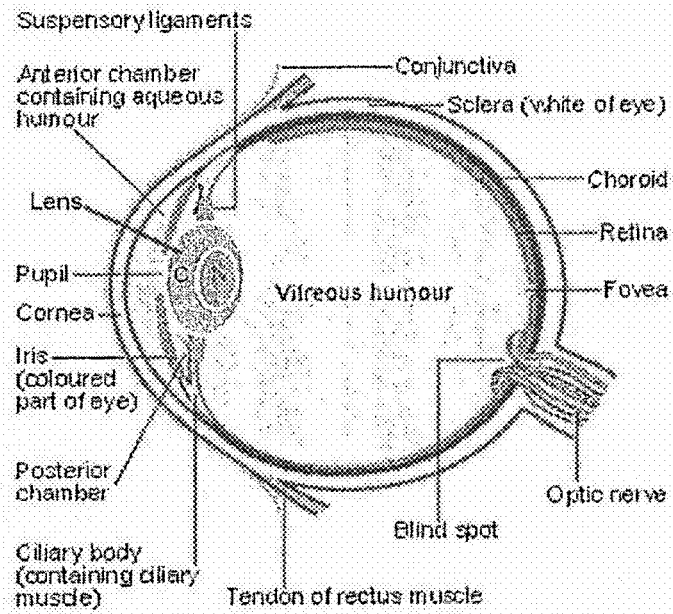
FIG. 2 is a schematic of the changes in lens shape when the ciliary muscle is relaxed for near vision (FIG. 2A) and contracted for far vision (FIG. 2B).
Figure 2B:
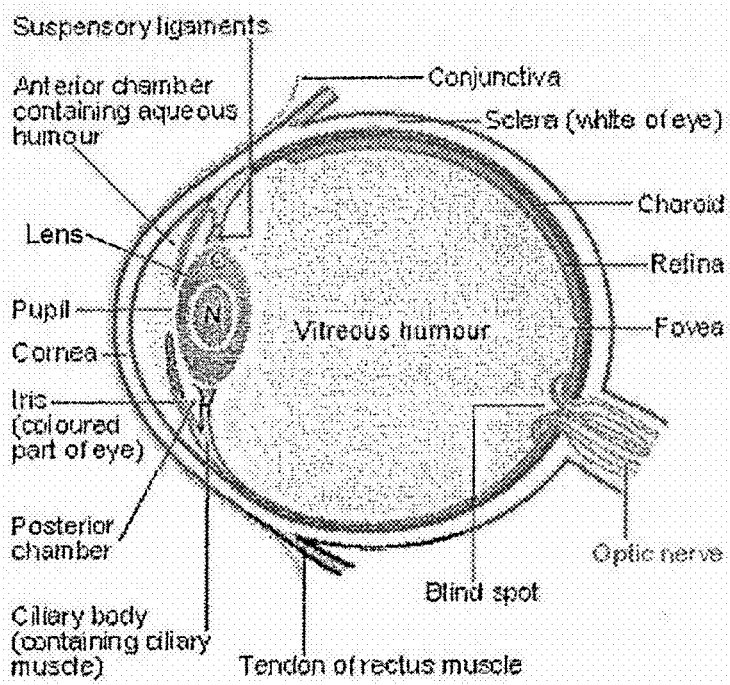

Agents, compositions, and methods are provided that can prevent, reduce, reverse, and/or slow the rate of lens growth, oxidative damage, and/or disulfide bond formation. These agents, compositions, and methods may thus effectively prevent or treat presbyopia and/or cataract. Also provided are compounds and methods that can affect one or more of: disulfide bond formation in lens membranes and membrane associated proteins, lens growth, lens cystine and lipoic acid concentrations, cellular and lens fiber redox state, cellular elasticity, and lens transparency. These compounds and methods may thus effectively prevent or treat presbyopia and/or cataract.

Dithiol Compounds

In some embodiments, the agents described herein are dithiol compounds or dithiol derivatives. The dithiol compounds and dithiol derivatives are referred collectively herein as agents. Dithiol compounds contain at least two sulfur atoms, preferably exactly two sulfur atoms, while dithiol derivatives include a selenium or sulfonic group in place of one or more sulfur atoms of a dithiol compound. Thus, in one embodiment, the agent has at least two components, each independently selected from a sulfur atom, a selenium atom, and a sulfonic group. In another embodiment, the agent has at least two components, each independently selected from a sulfur atom and a selenium atom. The agents can be on the backbone and/or the substituents of the compound.

The agents can be cyclical, e.g., a five- or six-membered heterocycle, or non-cyclical. Exemplary five-membered heterocycles (designated by Formula 5) include, but are not limited to:

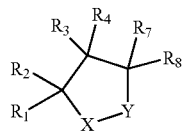

Formula 5-A

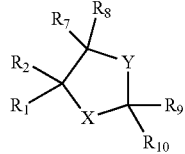

Formula 5-B

Exemplary six-membered heterocycles (designated by Formula 6) include, but are not limited to:

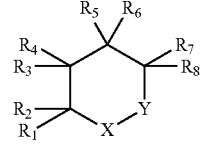

Formula 6-A

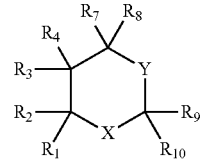

Formula 6-B

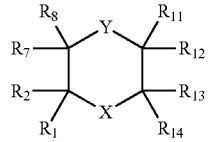

Formula 6-C

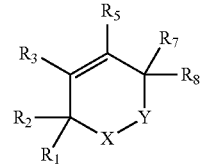

Formula 6-D

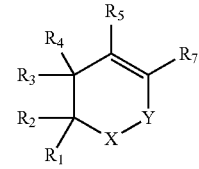

Formula 6-E

Exemplary non-cyclical agents (designated by NC) include, but are not limited to:

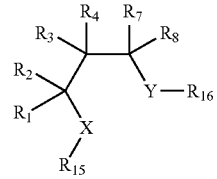

Formula 5-NC

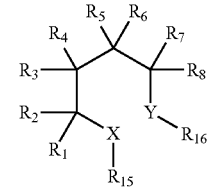

Formula 6-NC

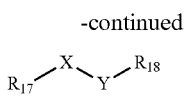

Formula NC

The agents can be classified in various ways. For example, the agent can be encompassed by any one of the following classification groups:
5-A, 5-B, 6-A, 6-B, 6-C, 6-D, and 6-E: cyclical
5-NC, 6-NC, and NC: non-cyclical
5-A, 5-B, and 5-NC: 5-membered
5-A and 5-B: 5-membered cyclical
6-A, 6-B, 6-C, 6-D, 6-E, and 6-NC: 6-membered
6-A, 6-B, 6-C, 6-D, and 6-E: 6-membered cyclical
5-A and 5-NC: potential hydrogenation pair
6-A and 6-NC: potential hydrogenation pair
5-NC and 6-NC: potential hydrogenation products
5-A, 6-A, 6-D, and 6-E: adjacent thiols
5-A and 6-A: adjacent thiols, saturated ring
6-A, 6-D, and 6-E: adjacent thiols, 6-membered cyclical
5-B, 6-B, and 6-C: non-adjacent thiols
5-B and 6-B: 1,3 thiols
6-A, 6-B, and 6-C: dithanes
6-D and 6-E: dithiines
or the agents can be classified by any individual formula.

For each of the agents, X and Y are independently selected from a sulfur atom, a selenium atom, and a sulfonic group. Preferably, at least one of X and Y is sulfur. In one embodiment, X and Y are both sulfur. In another embodiment, one of X and Y is sulfur, and the other is sulfur or selenium. In yet another embodiment, one of X and Y is sulfur, and the other is selenium. In one embodiment, the agent is a seleno derivative where at least one of X and Y is selenium. Without being bound by theory, it is believed that the selenium atom advantageously helps to overcome redox potential.

Each R group is independently selected from —H, —OH, —OAc, —OR, —SR, —CO$_2$R, an electron withdrawing group, and a linear or branched C$_{1-18}$ alkane or alkene optionally substituted by one or more ether, ester, carboxylic acid, phosphate, amide, and/or amine groups. In another embodiment, each R group is independently —H, —OH, —OAc, —CO$_2$CH$_3$, or a linear C$_{1-18}$ alkane or alkene optionally having a distal terminal that is —COOH, —NH$_2$, —CO$_2$CH$_3$, or —CO$_2$CH$_2$CH$_3$.

In one embodiment, various agents can be prepared by altering the placement of a particular R group. Any particular R group can be attached, for example, to a carbon adjacent to a thiol group (sulfur atom) or thiol derivative (e.g., selenium or sulfonic group). R$_1$, R$_2$, R$_7$, R$_8$, R$_9$, R$_{10}$, R$_{11}$, R$_{12}$, R$_{13}$, and R$_{14}$ represent such thiol-adjacent positions. In another embodiment, an R group can be attached to a carbon not adjacent to a thiol group or thiol derivative. R$_3$, R$_4$, R$_5$, and R$_6$ represent such non-adjacent positions. In yet another embodiment, an R group can be attached directly to a thiol group or thiol derivative. R$_{15}$, R$_{16}$, R$_{17}$, and R$_{18}$ represent such direct thiol attachments.

In one embodiment, one, two, or more R groups are —H. In some embodiments of Formula 5-NC and 6-NC, both of R$_{15}$ and R$_{16}$ are —H.

In one embodiment, one, two, or more R groups are —OH.

In another embodiment, one, two, or more R groups are —OAc. Without being bound by theory, the addition of an acetate ester (—OAc) is believed to improve corneal permeability, which is especially beneficial for the treatment of presbyopia.

In yet another embodiment, each R group is independently —H, —OH, —OAc, or —CH$_3$. In another embodiment, one R group is a chain substituent, and the remaining R groups are independently —H, —OH, —OAc, or —CH$_3$.

In one embodiment, the agent has the structure of Formula 6-A:

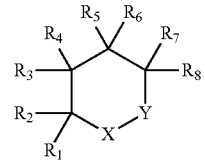

wherein each of R$_1$, R$_2$, R$_7$, and R$_8$ is —H; and
R$_3$, R$_4$, R$_5$, and R$_6$ are independently selected from —H, —OH, and —OAc.

In another embodiment, one, two, or more R groups are —CO$_2$R. In another embodiment, one, two, or more R groups are —OR. In particular embodiments, the R of —CO$_2$R or —OR is a lower alkyl group having 1-8 carbons. In one embodiment, —CO$_2$R is —CO$_2$CH$_3$.

In one embodiment, the agent includes a C$_{1-18}$ alkane or alkene, which are collectively referred to herein as chain substituents. The agent can be modified by altering the length of the chain substituent(s). Without being bound by theory, longer chains are believed to render the compound more hydrophobic, more lipid soluble, and thus more easily transported across the cell membrane. The length of the chain is limited by the lipid membrane width; a chain longer than the membrane width is likely to cause saponification. Shorter chains, on the other hand, and other similarly small substituents such as —OH and —CO$_2$CH$_3$, may be useful for preparing agents that are active in the cytosol and do not require membrane permeability. Substituent size and its concomitant effect on solubility also affect formulation considerations. For example, a hydrophobic drug may be more difficult to formulate as an administratable solution, but it may be more easily formulated for sustained release delivery systems.

In one embodiment, the agent includes a linear C$_{1-18}$ alkane or alkene, which are collectively referred to herein as linear substituents. Without being bound by theory, linear substituents are more commonly found in natural compounds, so agents including linear substituents may be better tolerated by the body. However, branched substituents may also be used. The linear substituent can be, for example, attached to a carbon adjacent to a thiol group (sulfur atom) or thiol derivative (e.g., selenium or sulfonic group). In other words, one or more of R$_1$, R$_2$, R$_7$, R$_8$, R$_9$, R$_{10}$, R$_{11}$, R$_{12}$, R$_{13}$, and R$_{14}$ can be a linear substituent. In another embodiment, one or more of R$_3$, R$_4$, R$_5$, and R$_6$ can be a linear substituent.

In one embodiment, a chain substituent includes an ether, ester, carboxylic acid, phosphate, and/or amine group at the distal terminal of a chain. In one embodiment, the distal terminal is a carboxylic acid or an amine. In another embodiment, one, two, or more R groups are —(CH$_2$)$_{2-10}$CO$_2$H or —(CH$_2$)$_{2-10}$NH$_2$. Without being bound by theory, it is believed that carboxylic acid and amine terminals provide attachment points for natural amino acids to form peptide amide bonds. For example, the carboxylic acid terminal of exemplary agent lipoic acid is often covalently attached to the amine lysine side chain of the active mitochondrial enzyme. The mitochondrial functionality of lipoic acid is discussed in further detail below.

In another embodiment, the distal terminal of a chain substituent is an ester, e.g., methyl or ethyl ester. In one embodiment, one, two, or more R groups are —$(CH_2)_{2-10}CO_2CH_3$ or —$(CH_2)_{2-10}CO_2CH_2CH_3$. Without being bound by theory, esterification is one way to modify the delivery of the pharmaceutical agent since the agent is inhibited from entering the cell until the ester is broken, e.g., by naturally occurring esterases. In this way, an esterified agent can serve as a prodrug that can be converted to an active form.

In one embodiment, the linear substituent is a linear $C_{1-18}$, $C_{2-12}$, $C_{2-10}$, $C_{2-8}$, $C_{2-6}$, $C_{4-6}$, $C_{5-6}$, or $C_5$ alkane. Exemplary agents including a linear alkane substituent are provided in the table below. The remaining undefined R groups are independently —H, —OH, —OAc, or —$CH_3$.

TABLE 1

| Formula | X, Y | R |
|---|---|---|
| 5-A; 5-NC; or 6-B | X is S and Y is S | $R_1$ or $R_3$ is: —$(CH_2)_{3-10}CO_2H$; —$(CH_2)_{3-10}CO_2CH_3$; or —$(CH_2)_{3-10}CO_2CH_2CH_3$ |
| 5-A; 5-NC; or 6-B | X is S and Y is S; X is S and Y is Se; or X is Se and Y is S | $R_1$ or $R_3$ is: —$(CH_2)_{1-2}CO_2H$; —$(CH_2)_{1-2}CO_2CH_3$; —$(CH_2)_{1-2}CO_2CH_2CH_3$; or —$(CH_2)_{2-10}NH_2$ |
| 5-A 5-NC 6-B | X is S and Y is Se; or X is Se and Y is S | $R_1$ or $R_3$ is: —$(CH_2)_{3-10}CO_2H$; —$(CH_2)_{3-10}CO_2CH_3$; or —$(CH_2)_{3-10}CO_2CH_2CH_3$ |
| 6-A 6-NC | X is S and Y is S; X is S and Y is Se; or X is Se and Y is S | $R_1$ or $R_3$ is: —$(CH_2)_{2-10}CO_2H$; —$(CH_2)_{2-10}NH_2$; —$(CH_2)_{2-10}CO_2CH_3$; or —$(CH_2)_{2-10}CO_2CH_2CH_3$ |
| 5-B | X is S and Y is S; X is S and Y is Se; or X is Se and Y is S | $R_1$ or $R_9$ is: —$(CH_2)_{2-10}CO_2H$; —$(CH_2)_{2-10}NH_2$; —$(CH_2)_{2-10}CO_2CH_3$; or —$(CH_2)_{2-10}CO_2CH_2CH_3$ |
| 6-D 6-E | X is S and Y is S; X is S and Y is Se; or X is Se and Y is S | $R_1$, $R_3$, $R_5$, or $R_7$ is: —$(CH_2)_{2-10}CO_2H$; —$(CH_2)_{2-10}NH_2$; —$(CH_2)_{2-10}CO_2CH_3$; or —$(CH_2)_{2-10}CO_2CH_2CH_3$ |

Exemplary agent lipoic acid and some derivatives thereof include a linear alkane with a carboxylic acid terminal:

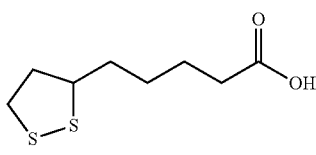

Lipoic acid

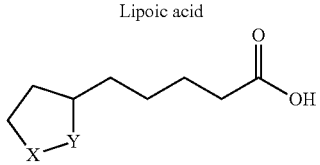

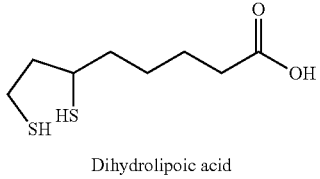

Dihydrolipoic acid

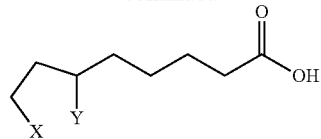

In one embodiment, the agent is lipoic acid (5-(1,2-dithiolan-3-yl)pentanoic acid), particularly alpha lipoic acid. In another embodiment, the agent is a lipoic acid derivative. Preferred lipoic acid derivatives do not interfere with the natural cellular mechanisms utilizing lipoic acid and/or dihydrolipoic acid. The agents described herein include those having relatively minor modifications to lipoic acid (e.g., altering chain length, replacing a sulfur atom with selenium) such that naturally occurring mitochondrial mechanisms can utilize either lipoic acid or the derivative. Agents having minor modifications may be relatively substitutable for lipoic acid and do not interfere with mitochondrial activity. Thus, in one embodiment, the agent functionally mimics lipoic acid in terms of redox activity and/or mitochondrial activity, but is not structurally identical to lipoic acid. Other agents include those having more major modifications to lipoic acid (e.g., altering chain placement). Such major modifications may render the agent unrecognizable to the mitochondria, thus avoiding interference with cellular mechanisms. In this way, both minor and major modifications can avoid mitochondrial interference. Mitochondrial interference, or the lack thereof, can be verified by in vitro testing according to methods known in the art such as, for example, a JC-1 Mitochondrial Membrane Potential Assay Kit (Cell Tech. Inc.). One of ordinary skill in the art could balance the strength of the reducing agent, which is believed to be responsible for the therapeutic effect, against mitochondrial interference, which might cause adverse effects. Exemplary lipoic acid derivatives include, but are not limited to: 5-(1,2-thiaselenolan-5-yl)pentanoic acid and 5-(1,2-thiaselenolan-3-yl)pentanoic acid.

In another embodiment, the linear substituent is a linear $C_{1-18}$, $C_{1-8}$, $C_{5-15}$, $C_{10-18}$, or $C_{10-16}$, or $C_{12-14}$ alkene. The alkene chain can have one, two, three, or more double bonds. Without being bound by theory, linear alkenes of relatively longer length, e.g., $C_{10-18}$, particularly those including a carboxylic acid or ester group, may exhibit advantageous properties similar to a fatty acid group.

Alkenes, including those of shorter lengths, are also useful, especially for embodiments of Formula NC. For example, in one embodiment, each of $R_{17}$ and $R_{18}$ is independently selected from $C_{2-8}$, $C_{2-6}$, $C_{3-4}$, $C_{3-5}$, or $C_3$ alkenes. In another embodiment of Formula NC, $R_{17}$ and/or $R_{18}$ is an —$SC_{2-8}$ alkene.

A chain substituent can include more than one ether, ester, carboxylic acid, phosphate, or amine substituent. For example, one exemplary agent is cystine (3,3'-disulanedylbis (2-aminopropanoic acid)), which includes both carboxylic acid and amine substituents. In one embodiment, the agent is cystine or a derivative thereof such as the exemplary derivative shown below:

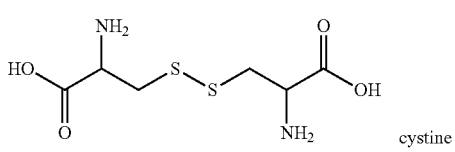

cystine

-continued

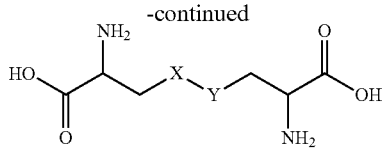

In another embodiment, R is an electron withdrawing group, which can decrease the pKa of the agent. Electron withdrawing groups include, but are not limited to: halogens (e.g., F, Cl), nitriles (CN), carboxylic acids (COOH), and carbonyls (CO).

In one embodiment, the agent is an allium oil antioxidant or a derivative thereof. Allium oil antioxidants are advantageously natural, nontoxic, and lipid soluble. Some have been studied as potential cytostatic agents for the treatment of atherlerosclerosis, cancer, etc. Without being bound be theory, the cytostatic properties may also provide advantageous efficacy in the context of ocular diseases caused by lens growth, including presbyopia and cataract.

One class of allium oil antioxidants is the dithiines. Exemplary dithiines include, but are not limited to:

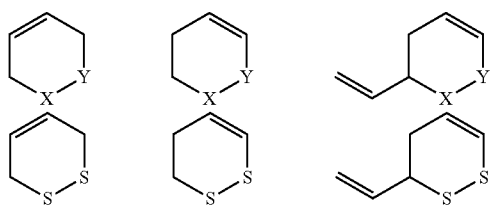

3,6-dihydro-1,2-dithiine   3,4-dihydro-1,2-dithiine   3-vinyl-[4H]-1,2-dithiine

Other allium oil antioxidants include, but are not limited to:

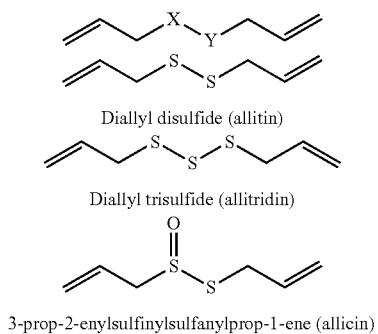

Diallyl disulfide (allitin)

Diallyl trisulfide (allitridin)

3-prop-2-enylsulfinylsulfanylprop-1-ene (allicin)

In another embodiment, the agent can be a dithiane or a derivative thereof. Without being bound by theory, it is believed that dithianes increase cellular non-protein SH, a primary objective in the treatment of presbyopia. Exemplary dithianes include, but are not limited to:

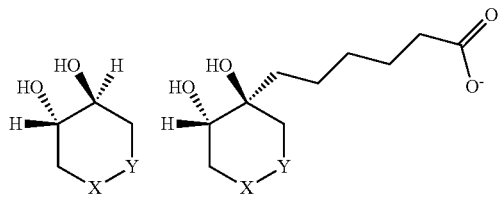

-continued

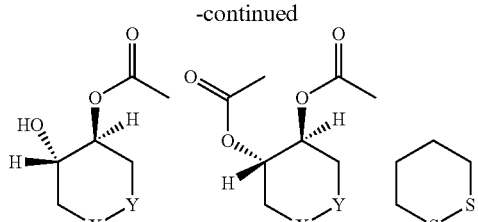

1,2-dithiane

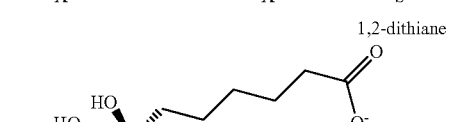

6-((4R,5R)-4,5-dihydroxy-1,2-dithian-4-yl) hexanoate

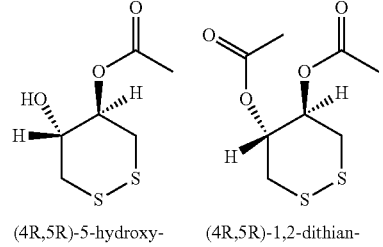

(4R,5R)-5-hydroxy-1,2-dithian-4-yl acetate (4R,5R)-1,2-dithian-4,5-diyl diacetate In one embodiment, the agent is a derivative of dithiothreitol (DTT) such as trans-4,5-dihydroxy-1,2-dithiane, also referred to herein as "non-lethal DTT":

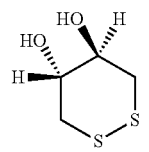 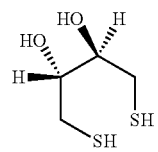

Trans-4,5-dihydroxy-1,2-dithiane (Non-lethal DTT)

Dithiothreitol (DTT)

Both DTI and non-lethal DTT possess potent antioxidant properties, but non-lethal DTT possesses the further advantage of reduced toxicity thereby being more favorable for use in in vivo settings.

Caged Compounds

In one embodiment, the invention provides a compound comprising an active agent X removably linked to at least one cage.

The active agent X is any agent capable of inducing a therapeutic effect as described above. Exemplary reducing agents include, but are not limited to, lipoic acid, cystine, glutathione, ascorbic acid, Vitamin E, tetraethylthiuram disulfyl, ophthalmic acid, inositol, beta-carbolines, reducing thiol derivatives, reducing sulfur derivatives, thiodisulfide exchange reaction agents such as dithiothreitol (DTT), trialkylphosphine, and tris[2-carboxyethyl]phosphine hydrochloride (TCEP.HCl), thioredoxin, and bis(mercaptoacetyl) hydrazine derivatives, as well as variations thereof. See, e.g., co-pending US 2008/0139990; see also U.S. Pat. Nos. 5,688,828 and 5,686,450. Preferably, the active agent is a reducing agent that is capable of reducing disulfide bonds, particularly disulfide bond formation in lens membranes and membrane associated proteins. Accordingly, particularly preferred active agents are capable of entering into the lens epithelial cells.

Figure 3:
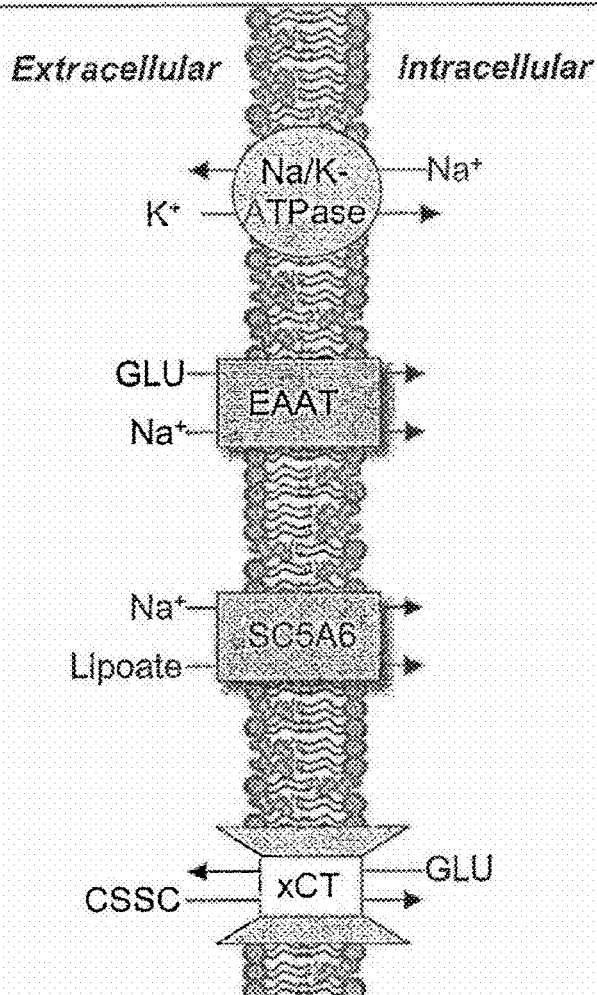
FIG. 3 depicts the cellular transport mechanism of cystine (CSSC) and lipoate into lens epithelial cells and fibers using intracellular glutamate and the sodium gradient.

In one embodiment, the compound enters the lens epithelial cells using a naturally occurring transport mechanism. For example, lipoic acid and cystine enter lens cells via specific plasma membrane symporters and antiporters. The lens epithelium and fibers have transporters for lipoic acid and cystine that depend upon the sodium gradient for uptake into cells, where the agents are reduced to dihydrolipoic acid and cysteine, respectively (FIG. 3). By using lipoic acid- or cystine-based compounds, one can utilize a naturally occurring transport mechanism to deliver the agents to the lens cells.

The transport mechanism operates as follows: In the lens, there are three Na,K-ATPase isozymes that use the energy of ATP hydrolysis for the electrogenic exchange of three intracellular sodium ions ($Na^+$) for two extracellular potassium ions ($K^+$). The result is a gradient for $Na^+$ where $[Na^+]_{intracellular} < [Na^+]_{extracellular}$ and a gradient for $K^+$ where $[K^+]_{intracellular} > [K^+]_{extracellular}$. The α2β2 isozyme of Na,K-ATPase maintains the sodium gradient in lens fibers. The α1β1 and α3β2 Na,K-ATPase isozymes maintain the sodium gradient in the lens epithelium.

Excitatory amino acid transporters EAAT1-EAAT5 are responsible for uptake of glutamate in the lens. EAATs are high affinity sodium-dependent glutamate (GLU, FIG. 3) symporters whose efficiency is regulated by the sodium gradient's steepness, i.e., the steeper the $Na^+$ gradient, the faster the uptake of extracellular glutamic acid. EAATs are highest in lens epithelium and cortical fibers and lowest, almost non-existent, in nuclear fibers.

The glutamate gradient created by the EAATs ($[GLU]_{intracellular} > [GLU]_{extracellular}$) is used for the exchange of extracellular cystine (CSSC, FIG. 3) via the glutamate-cystine antiporter (xCT). xCT is cytoplasmic in superficial lens cortical fibers and an integral membrane protein in lens nuclear fibers. This glutamate-cystine exchange is critical for the lens cell's oxidative status as demonstrated by mice deficient in xCT, which display redox imbalances. xCT requires the anionic deprotonated carboxyl groups of cystine for exchange.

The sodium-dependent multivitamin transporter (symporter), SC5A6 (SMVT), is responsible for lipoate influx into cells. Like the EAATs, SC5A6 is regulated by the steepness of the $Na^+$ gradient. Again, the carboxylate anion is required for transport. Lens cortical fibers are one target for the lipoic acid-based compounds described herein because these cells express SC5A6 and its mRNA is found there.

In one embodiment, the active agent is lipoic acid, especially alpha-lipoic acid, or a derivative thereof. Lipoic acid-based active agents include, but are not limited to, 5-(1,2-dithiolan-3-yl)pentanoic acid (lipoic acid); 6,8-dimercaptooctanoic acid (dihydrolipoic acid); and dihydrolipoate. Lipoic acid not only advantageously utilizes a naturally occurring transport mechanism, but may also be effective to combat prevent and/or treat a wide variety of cell damage and/or disorder types.

Lipoic acid functions as an acyl group transferring factor in aerobic metabolism shuttling acyl groups between thiamine pyrophosphate (ThPP) and Coenzyme A (CoA). In the mitochondria, lipoic acid acts as a co-factor in the glycine cleavage, forming 2-oxoacid dehydrogenase, pyruvate dehydrogenase, branched chain oxoacid dehydrogenase and acetoin complexes. Lipoic acid is synthesized in the mitochondria. Lipoic acid levels are adequate in differentiating fibers containing mitochondria (superficial cortex), but fall precipitously in fibers of the deeper cortex where cellular organelles have been lost.

Exogenous lipoic acid, with a redox potential of –0.29V, acts as an antioxidant. In lenses treated with lipoic acid, the lens fibers in the process of losing mitochondria and those fibers devoid of mitochondria can benefit from the antioxidant properties of the agent.

Lipoic acid may also prevent symptoms associated with vitamin E deficiency, reverse $H_2O_2$-dependent inhibition of alpha-ketoglutarate dehydrogenase, and prevents reserpine-induced oxidative stress in the striatum, hyperglycemia-induced SH-group oxidation in erythrocyte membranes, and buthionine sulfoximine-induced cataract formation. Lipoic acid may also reverse or prevent age dependent memory loss and improve hemodynamic properties following ischemia-reperfusion in heart without improvement of cardiac electrophysiological properties. Lipoic acid changes cellular redox status, thus stimulating glucose uptake in adipocytes and skeletal muscle presumably by increasing plasma membrane levels of GLUT4. Finally, lipoic acid ameliorates insulin resistance in the Goto-Kakizaki rat model of type II diabetes.

In another embodiment, the active agent is cystine or a derivative thereof. Cystine-based active agents include, but are not limited to, 3,3'-disulanedylbis(2-aminopropanoic acid) (cystine) and 2-amino-3-mercaptopropanoic acid (cysteine). Like lipoic acid, cystine not only advantageously utilizes a naturally occurring transport mechanism, but may also be effective to combat prevent and/or treat a wide variety of cell damage and/or disorder types.

Figure 4A:
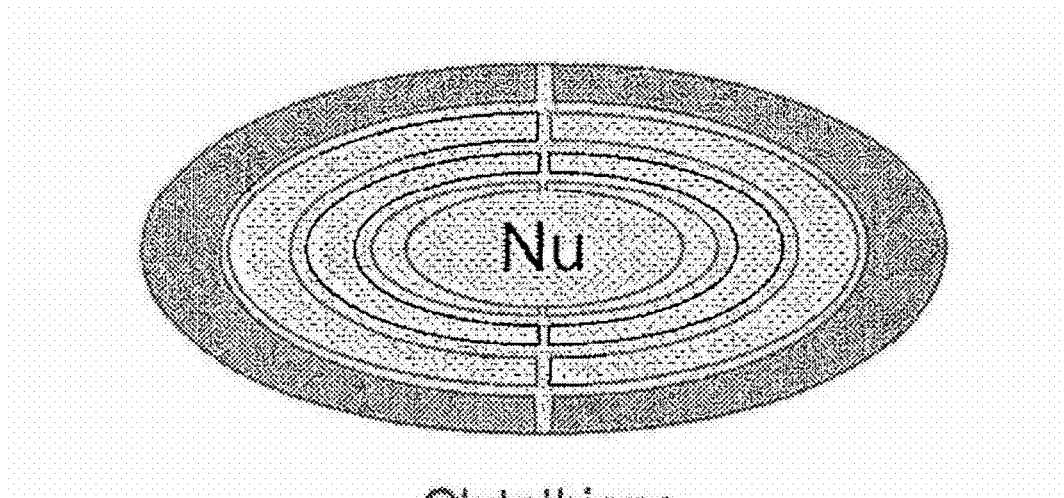
FIG. 4 depicts the glutathione concentration (FIG. 4A) and cystine concentration (FIG. 4B) in the eye.
Figure 4B:
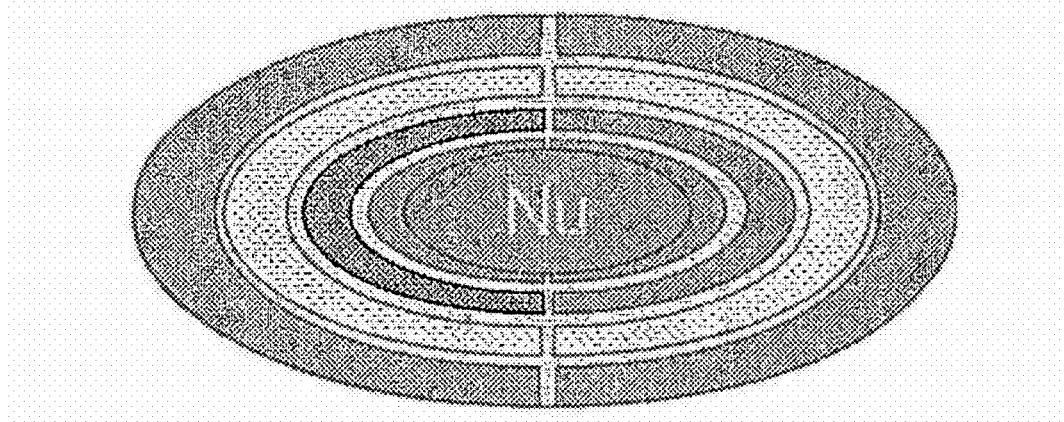

The cysteine/cystine redox couple (CSH/CSSC) plays multiple roles in oxidative stress response as well as acts as a source of cysteine for the synthesis of glutathione GSH. GSH is the electron-donating compound of the GSH/GSSG redox couple. In plasma, the redox state of the CSH/CSSC and GSH/GSSG couples vary diurnally. The redox states of these two couples do not vary concomitantly, i.e., each couple has a unique maximum and nadir. The intracellular redox potentials of GSH:GSSG and CSH:CSSC regulate cellular proliferation, differentiation, and programmed cell death. Total glutathione concentration (GSH+GSSG) is highest in the epithelium and superficial cortex as depicted by the darker area in FIG. 4A. Total Cys concentration (CSH+CSSC), on the other hand, is higher in the superficial cortex and lens nucleus than in the deep cortex, i.e., a bimodal distribution, as shown by the darker area in FIG. 4B. GSH is senses and protects against oxidative stress in the lens epithelium and superficial fibers. However, the low levels of GSH deeper in the cortex suggest a role for the GSH/GSSG redox couple in the regulation of mitochondrial disappearance during fiber differentiation. In the lens nucleus, the CSH/CSSC couple is most likely involved in protection against oxidative stress. The fibers of the deep cortex appear to be deficient in both the glutathione and cysteine couple.

The agents disclosed herein can be used to selectively increase lens cystine levels in deep anterior cortex, thereby beneficially changing the redox potential of extracellular and intracellular space, altering disulfide levels, decreasing lens stiffness, decreasing the potential for, or existence of, high molecular weight protein aggregates, and/or reducing cataract formation. These beneficial effects can be demonstrated in lens epithelial cell and lens organ culture models.

In another embodiment, the active agents include seleno-substituted agents. Without being bound by theory, it is believed that including selenium in the active agent can improve redox potential compared to the same agent without selenium. The selenium derivative can thus take advantage of the intracellular redox potential of the lens.

Accordingly, the active agent can be a lipoic acid or cystine derivative including selenium. In one embodiment, the active agent is a seleno-lipoic acid-based agent such as 5-(1,2-thiaselenolan-5-yl)pentanoic acid or 5-(1,2-thiaselenolan-3-yl)pentanoic acid. In another embodiment, the active agent is a seleno-cystine-based agent such as 2-amino-3-hydroselenopropanoic acid.

In one embodiment, the active agent is 5-(1,2-dithiolan-3-yl)pentanoic acid; 5-(1,2-thiaselenolan-5-yl)pentanoic acid; 5-(1,2-thiaselenolan-3-yl)pentanoic acid; 6,8-dimercaptooctanoic acid; dihydrolipoate; 3,3'-disulanedylbis(2-aminopropanoic acid); 2-amino-3-mercaptopropanoic acid; or 2-amino-3-hydroselenopropanoic acid.

In another embodiment, the active agent is 5-(1,2-dithiolan-3-yl)pentanoic acid; 5-(1,2-thiaselenolan-5-yl)pentanoic acid; 5-(1,2-thiaselenolan-3-yl)pentanoic acid; 6,8-dimercaptooctanoic acid; dihydrolipoate; 3,3'-disulanedylbis(2-aminopropanoic acid); or 2-amino-3-hydroselenopropanoic acid.

In one embodiment, the active agent is lipoic acid or a derivative thereof. For example, the active agent can be 5-(1,2-dithiolan-3-yl)pentanoic acid; 5-(1,2-thiaselenolan-5-yl)pentanoic acid; 5-(1,2-thiaselenolan-3-yl)pentanoic acid; 6,8-dimercaptooctanoic acid; or dihydrolipoate. In another embodiment, the active agent is 5-(1,2-dithiolan-3-yl)pentanoic acid or 6,8-dimercaptooctanoic acid. In yet another embodiment, the active agent is 5-(1,2-dithiolan-3-yl)pentanoic acid.

In another embodiment, the active agent is cystine or a derivative thereof. For example, the active agent can be 3,3'-disulanedylbis(2-aminopropanoic acid); 2-amino-3-mercaptopropanoic acid; or 2-amino-3-hydroselenopropanoic acid. In yet another embodiment, the active agent can be 3,3'-disulanedylbis(2-aminopropanoic acid) or 2-amino-3-hydroselenopropanoic acid.

In some embodiments, the active agent is removably linked to at least one cage. The active agent may be linked to one, two, three, or more cages depending on the particular structure of the active agent and the cage(s).

A "cage" as used herein means a photolabile protecting group. The cage is linked to the active agent and is capable of being removed from the active agent by the application of light energy. Preferably, the cage is linked to the active agent in such a way as to render the agent biologically inactive. The agent can be activated by applying light to remove the cage. Because the cage is readily removed by light, one can control the time and/or place of the agent's activity. Exemplary cages and synthetic methods useful for the compounds herein include, but are not limited to those disclosed by U.S. Pat. No. 6,472,541 and Kao, J P. 2006. Caged Molecules: Principles and Practical Considerations. Curr Protoc Neurosci. Ch. 6:Unit 6.20. Specific exemplary cages include, but are not limited to, (6-nitrocoumarin-7-yl)methyl; N-(o-nitromandelyl)oxycarbonyl; p-hydroxyphenacyl; 7-Nitroindolinyl; 4-methoxy-7-nitroindolinyl; γ-(α-carboxy-2-nitrobenzyl); 6-bromo-7-hydroxycoumarin; naphthalene groups, e.g., (6-hydroxy-3-oxo-3,4-dihydronaphthalen-1-yl)methyl); quinoline-2-one; xanthene; thioxanthene; selenoxanthene; anthracene; and nitroso groups.

In one embodiment, the cage is a coumarin group. Coumarin cages can be advantageous in that they exhibit low toxicity. Also, the coumarin cages may be removed with light in the UVA range, as opposed to many other photolabile cages that can only be removed with UVB light. In particular embodiments, the cage has the formula:

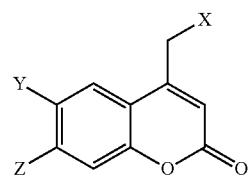

wherein Y is —H, —Br, —OCH$_3$, —OCH$_2$CO$_2$H, —OCH$_2$CO$_2$CH$_2$CH$_3$, —NH$_2$, —SO$_3$H, or —CH$_2$CO$_2$H; and Z is —H, —OH, —OCH$_3$, —O$_2$CCH$_3$, —O$_2$CCH$_2$CH$_3$, —CH$_2$CO$_2$H, —N(CH$_3$)$_2$, —N(CH$_2$CH$_3$)$_2$, —NH$_2$, or —SO$_3$H.

In a particular embodiment, the cage is a 7-hydroxy-coumarin-4-ylmethyl-carboxyl group (HC) or a 6-bromo-7-hydroxy-coumarin-4-ylmethyl-carboxyl group (BHC).

A cage can be attached to any charged or polar substituent of the agent. In one embodiment, a cage is attached to a carboxylate group, an amino group, or a sulfur atom of the active agent. When the cage is attached to an amino group of the active agent, it is preferably linked via a carboxylate group.

In one embodiment, the active agent is one of:

5-(1,2-dithiolan-3-yl)pentanoic acid (lipoic acid);

5-(1,2-thiaselenolan-5-yl)pentanoic acid;

5-(1,2-thiaselenolan-3-yl)pentanoic acid;

6,8-dimercaptooctanoic acid (dihydrolipoic acid);

3,3'-disulanedylbis(2-aminopropanoic acid) (cystine);

2-amino-3-mercaptopropanoic acid (cysteine);

2-amino-3-hydroselenopropanoic acid;

and a cage is linked to a carboxylate group on the active agent. In this embodiment, the lipoic acid- and cystine-based compounds are inhibited from uptake into the cells while the carboxyl group is caged. Once uncaged, the ionized form of the carboxyl group facilitates transport across the lens cell membrane.

In another embodiment, the active agent is one of:

2-amino-3-mercaptopropanoic acid, 2-amino-3-hydroselenopropanoic acid, 3,3'-disulanedylbis(2-aminopropanoic acid), and a cage is linked to an amino group of the active agent via —CO$_2$.

In another embodiment, the active agent is 2-amino-3-mercaptopropanoic acid or dihydrolipoate, and a cage is linked to a sulfur atom of the active agent.

Specific exemplary caged compounds include, but are not limited to:

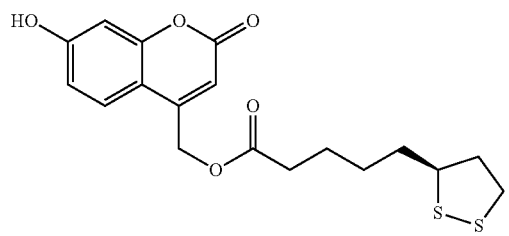

-continued

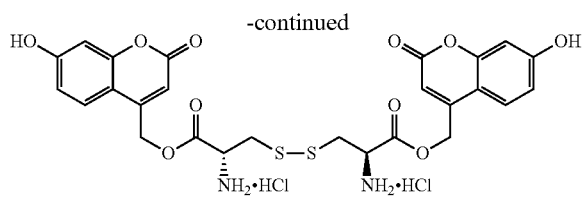

As the compounds described herein may have therapeutic uses as described in further detail below, it is preferable to select an active agent/cage combination with low toxicity. Furthermore, because the compound will be present in both the caged and uncaged form, it is preferable to select a combination such that any of its three forms—the caged compound, the active agent alone, and the cage alone—all exhibit low toxicity. For example, the coumarin cages described above have already been demonstrated to exhibit acceptable toxicology thresholds. For the 7-hydroxy-coumarin-4-ylm-ethyl-carboxyl group (HC), the median lethal dose ($LD_{50}$) is 30 mM. In fact, the cage can be cytostatic at lower concentrations. Without being bound by theory, it is believed that coumarin cages may exhibit a cytostatic effect on lenses to reduce lens cell growth, reduce whole lens growth, and/or increase GSH/GSSG ratios. Thus, the cage component itself may contribute to improving accommodative amplitude and/or postponing the onset of presbyopia.

Other biologically acceptable components (including each of active agent, cage, and caged compound) can be selected by in vitro toxicology testing. See, e.g., Example 5.

In one embodiment, a pharmaceutical composition can comprise cystine or a derivative thereof, optionally caged by a photolabile protecting group, and a pharmaceutically acceptable carrier. In another embodiment, the pharmaceutical composition contains caged cystine or a derivative thereof and a pharmaceutically acceptable carrier.

The compounds can also be administered with a chemical energy source, such as portion of glucose or NADPH, to facilitate reduction. The caged compound and chemical energy source can be co-formulated (e.g., prepared together in a single pharmaceutical formulation) or co-administered (administered simultaneously or consecutively in any order in individual formulations).

The compounds described herein can be employed in a method including the steps of: 1) providing a caged compound including an active agent removably linked to at least one cage, and 2) uncaging the active agent by applying light. The details of the caged compound are described above, while the details of light application are described below. Also, an exemplary uncaging method is provided below in Example 4.

The active agent can also be in a salt or ester form.

The active agent can be administered as a racemate or as an enantiomer. For example, lipoic acid and its derivatives are preferably administered to include the R form; cystine and its derivatives are preferably administered to include the L form. Synthetic methods to yield a racemate may be less expensive than stereo-specific processes including isolation/purification steps. On the other hand, administering a single enantiomer can lower the therapeutically effective amount, thus decreasing toxicity effects, for example, the toxicity effects of both the active agent and the accompanying cage.

The agents described herein are preferably reducing agents. For example, the agents can possess a redox potential $E_0'$ (V) of about −0.01 to about −1.0, about −0.1 to about −0.5, about −0.2 to about −0.4, or about −0.3. The agents described herein preferably exhibit an acceptable toxicity profile, e.g., a median lethal dose ($LD_{50}$) of at least 10 μM, at least 20 M, at least 40 M, or at least 1 mM. Toxicity can be assessed by any method known in the art such as, for example, viability of human umbilical vein endothelial cells (HUVEC, first passage) using the MultiTox-Fluor assay (Promega) or Live/Dead® assay (Invitrogen). Of course, agents selected as pharmaceutical agents for the treatment of presbyopia should exhibit both antioxidant efficacy (reducing power) as well as a desirable safety profile (low toxicity). Accordingly, in one embodiment, a screening method is provided whereby dithiol compounds or derivatives are tested for reducing power and/or toxicity. In another embodiment, a method includes screening dithiol compounds or dithiol derivatives for their ability to increase lens elasticity either in vitro or in vivo.

The agents or compounds described herein preferably exhibit favorable membrane permeability, specifically corneal permeability. Corneal penetration can be measured by methods known in the art, such as, for example, those disclosed in Kim et al. (2005) "Aqueous penetration and biological activity of moxifloxacin 0.5% ophthalmic solution and gatifloxacin 0.3% solution in cataract surgery patients" Ophthalmology 112(11):1992-96. In one embodiment, the agent enters the lens epithelial cells using a naturally occurring transport mechanism. For example, lipoic acid and cystine enter lens cells via specific plasma membrane symporters and antiporters. By using lipoic acid, cystine, or derivatives thereof, one can utilize a naturally occurring transport mechanism to deliver the agents or compounds to the lens cells.

In another embodiment, a pharmaceutical composition includes an agent or compound as described herein and a pharmaceutically acceptable carrier. The pharmaceutical composition may also contain one or more excipients as is well known in the art of pharmaceutical formulary. In one embodiment, the pharmaceutical composition is formulated for ocular use. That is, the pharmaceutically acceptable carrier and/or other excipients are selected to be compatible with, and suitable for, ocular use. Such carriers and excipients are well known in the art. The excipients may also be selected and/or formulated to improve the solubility of the compound. For example, the pharmaceutical composition can include one or more of emulsifiers, buffers, salts, preservatives, lubricants, polymers, solvents, and other known excipients for ocular pharmaceutical formulations. In one embodiment, the pharmaceutical composition includes an emulsifier and a buffered carrier such as Polysorbate 80 in HBSS (Hank's Balanced Salt Solution).

Methods of Using the Agents or Compounds

In another embodiment, the agents or compounds are employed in a method for treating ocular disease, e.g., presbyopia, by administering an effective amount of the agent. In another embodiment, the agents or compounds are employed in a method for preventing or reversing oxidative damage to cells, e.g., lens cells. In some embodiments, such a method includes the steps of: 1) administering a caged compound including an active agent removably linked to at least one cage, and 2) uncaging the active agent by applying light.

The agents or compounds can be applied to lenses or cells in vitro or in vivo. In one embodiment, the cells are in vivo. In either case, the cells can be ocular cells, e.g., lens cells. In one embodiment, the caged compound is administered to a lens, either in vitro or in vivo. Because oxidative damage has been implicated in other disorders including cancer, the caged compounds may prove useful for administration to any type of cell exhibiting or prone to oxidative damage.

The agents or compounds described herein can be formulated to achieve any delivery system known in the art such as immediate or sustained release delivery; systemic, ocular, or localized delivery; topical or injection delivery; prodrug or caged delivery systems, e.g., coumarin cages (as described, for example, in co-pending application U.S. Ser. No. 12/267, 260), etc.

The agents or compounds can be linked to, co-administered with, and/or co-formulated with other therapies such as other pharmaceutically active ingredients and/or energy sources (as described, for example, in co-pending application U.S. Ser. No. 11/946,659). In one embodiment, the agent is co-administered with chemical energy, such as, for example glucose-6-phosphate (G6P), NADPH, or glucose. In one embodiment, the agent or compound is activated by an endogenous chemical energy, e.g., endogenous glucose. For example, endogenous glucose can activate lipoic acid or a derivative thereof to dihydrolipoic acid (DHLA) or a corresponding derivative thereof.

The agents or compounds can be formulated as a pharmaceutically acceptable salt.

The agents or compounds can be administered to a lens by any route of administration including, but not limited to, topical, subtenons, subconjunctival, intracameral, intravitreal, or iontophoresis routes. In one embodiment, the agent or compound can be delivered topically, e.g., via an eye drop, gel, ointment, or salve. In other embodiments, the compound can be delivered via an acute delivery system, e.g., using nanotubes, local injection, micro-injection, syringe or scleral deposition, or ultrasound.

The method can further include a step of waiting for accumulation, i.e., delaying activation of the compound for a period of time, called the "accumulation period," to allow the compound to migrate to the desired location of activity and/or vacate undesired locations of activity. For ocular applications, for example, the method can include waiting for accumulation as the compound migrates through the corneal boundary and diffuses into the interstitial space throughout the lens tissue. The compounds preferably accumulate in the anterior chamber, aqueous humor, and lens. The accumulation period can be, e.g., about 1, 5, 10, 15, 20, 30, 40, 45, 50, 60 minutes or more, or even a matter of days, such as about 1 to about 10 days depending on the method of administration. In another embodiment, the accumulation period is about 30 to about 60 minutes, about 10 to about 30 minutes, about 5 to about 15 minutes, about 1 to about 10 minutes, or about 1 to about 5 minutes.

Once the compound has accumulated at the desired location of activity, the compound is uncaged (activated) by applying light. Additionally or alternatively, the light can be applied to only a localized area of the target. In some embodiment, light is applied using an LED or laser source, which advantageously enables spatial specificity to deliver light to a localized region. Additionally or alternatively, other optical tools for creating and/or improving spatial specificity can be used with the methods described herein. The light can be targeted to particular areas, e.g., areas exhibiting inelasticity, opacity, and/or proliferation, while leaving other areas unaffected. In one embodiment, the compound and/or light can be localized to the anterior central portion of the lens or along the cylindrical optical axis.

Light application releases the active agent within the "activation volume" to change the flexibility of the lens so that the restoring force of the lens capsule is able to form the lens to a maximal spherical shape with increased curvature. The "activation volume" would be limited only by the available dilation of the patient papillary area although a smaller area may suffice to restore accommodative amplitude.

Figure 5A:
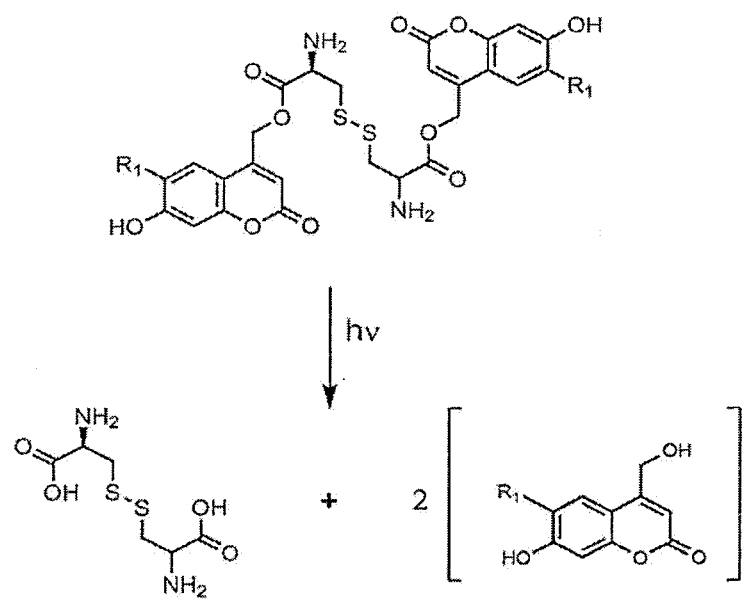
FIG. 5 shows the products of photolysis for caged cystine (FIG. 5A) and caged lipoic acid (FIG. 5B). $R_1$ is either H or Br.
Figure 5B:
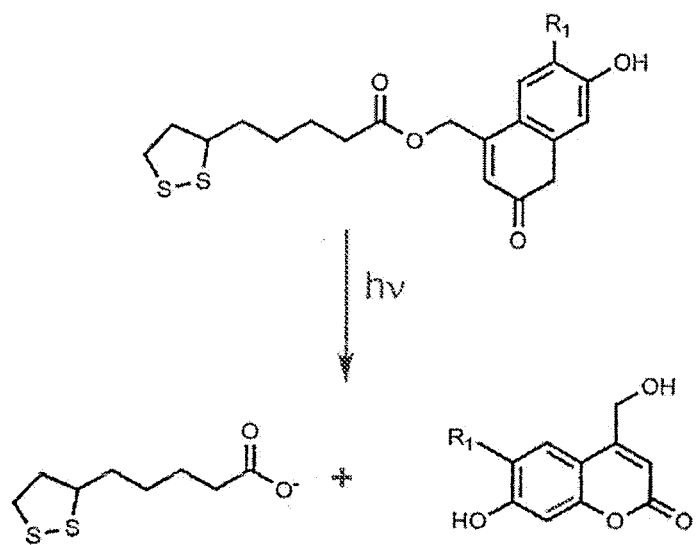

The light need not achieve 100% uncaging, but it should achieve a high enough degree of uncaging to achieve a therapeutic effect. Preferably, upon the application of light, at least about 50% of the caged compound portion administered is uncaged. More preferably, the caged compound becomes at least about 60, 70, 75, 80, 90, 95, 97, or 99 percent uncaged. Exemplary photolysis products are shown in FIG. 5.

The light should be strong enough to uncage the compound (that is, to remove the photolabile protecting group from the active agent), but mild enough to minimize collateral damage to surrounding cells and/or tissues. The light can be light of any wavelength including ultraviolet (less than about 400 nm), visible (about 380-750 nm), or infrared wavelengths (above about 750 nm).

In one embodiment, the compound can be uncaged using 1-photon or 2-photon photolysis. See, e.g., Example 4 and U.S. Pat. No. 6,472,541 Example 4. The photolabile 7-hydroxy-coumarin-4-ylmethyl-carboxyl-(HC) and 6-bromo-7-hydroxy-coumarin-4-ylmethyl-carboxyl (BHC) cages have large cross-sections for two-photon activation with a Ti:sapphire laser.

In another embodiment, the light is UVA light, e.g., a black light. The UVA light has a wavelength in the range of 315 to 400 nm, preferably about 325 to about 380 nm, about 330 to about 370, about 350 to about 375 nm, about 350 to about 380, or about 365 nm. In one embodiment, the UVA light has a wavelength of 365 nm±5, 10, 15, 20, 25, or 30 nm. UVA light is particularly advantageous at least in part because the less damaging wavelengths decrease the likelihood of collateral tissue damage. Also, from a practical standpoint, UVA light is inexpensive, especially compared to laser 2-photon sources. With these advantages in mind, coumarin cages may prove especially useful in the compounds and methods herein because the coumarin cages can be removed using UVA light. Other cages, in contrast, often require UVB light for removal. Because UVB light uses more damaging wavelengths (e.g., 280-315 nm), UVB light may increase the likelihood of collateral, cytotoxic tissue damage.

The method can further include a step of waiting for clearance, i.e., waiting for the remaining caged compound and/or its components to disappear after activation. This "clearance period" can be, e.g., about 1, 5, 10, 15, 20, 30, 40, 45, 50, 60 minutes or more, more preferably about 30 to about 60 minutes, about 10 to about 30 minutes, about 5 to about 15 minutes, about 1 to about 10 minutes, or about 1 to about 5 minutes.

The methods preferably utilize a therapeutically effective amount of the compound. The term "therapeutically effective amount" means an amount that is capable (in the active form) of preventing, reducing, reversing, and/or slowing the rate of oxidative damage. For ocular applications, a therapeutically effective amount may be determined by measuring clinical outcomes including, but not limited to, the elasticity, stiffness, viscosity, density, or opacity of a lens.

The term "effective amount" means an amount that is capable of preventing, reducing, reversing, and/or slowing the rate of oxidative damage. For ocular applications, a therapeutically effective amount may be determined by measuring clinical outcomes including, but not limited to, the elasticity, stiffness, viscosity, density, or opacity of a lens.

Figure 6:
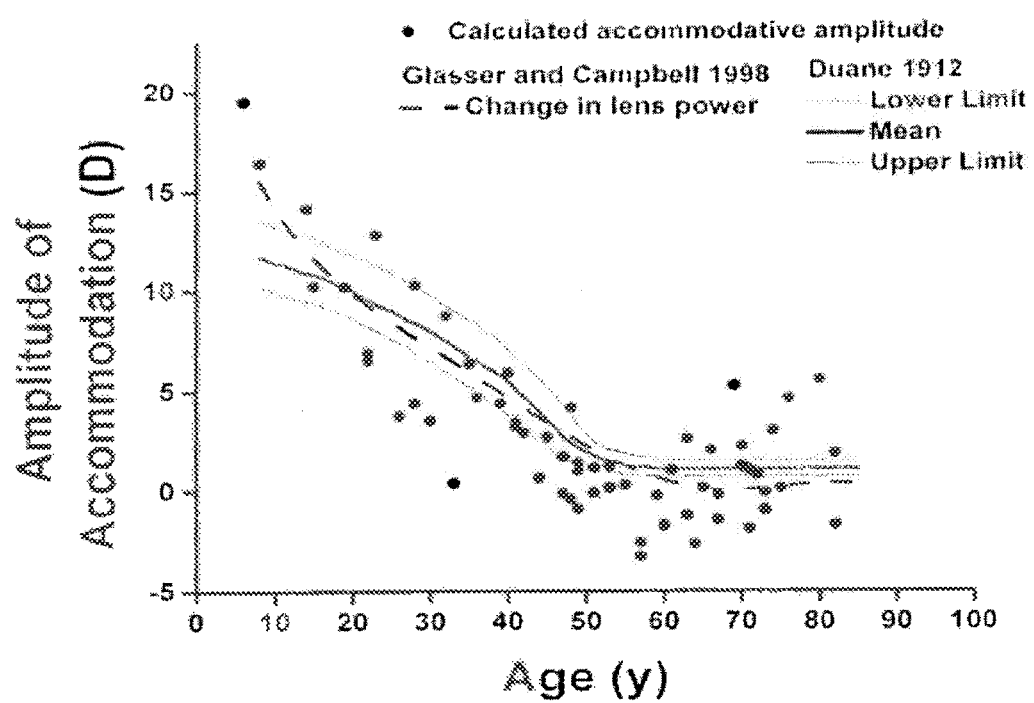
FIG. 6 depicts the accommodative amplitude in diopters (D) of an untreated human lens as a function of age in years. Borja, D et al. 2008. Optical Power of the Isolated Human Crystalline Lens. Invest Ophthalmol V is Sci 49(6):2541-8. Borja et al. calculated the maximum possible accommodative amplitude of each measured lens power data point (n=65). As shown, there is good agreement between the age-dependent loss of accommodation and the maximum amplitude of accommodation calculated from the isolated lens power.

Lens elasticity decreases with age and is a primary diagnostic and causative factor for presbyopia. Lens elasticity can be measured as accommodative amplitude in diopters (D). FIG. 6 depicts the average elasticity in diopters of an untreated human lens as a function of age in years. The lower the value of D, the less elastic the lens. In one embodiment, the agents or compounds described herein can decrease and/or maintain D at a value that is greater than the D value exhibited by an untreated lens of about the same age. In other words, the agents or compounds can keep accommodative amplitude "above the line" depicted in FIG. 6 (the solid line is mean accommodative amplitude). In one embodiment, D is increased and/or maintained at a value about 2, 5, 7, 10, 15, 25, 50, 100, 150, or 200 percent above the line. However, as individual lenses may differ with respect to average values, another embodiment provides any increase in accommodative amplitude, maintenance of accommodative amplitude, or reduction in the rate of decline of accommodative amplitude (i.e., reduction in the rate of decrease in diopters) for an individual lens compared to the accommodative amplitude of the same lens before treatment. Accordingly, in another embodiment, the methods provide an increase in accommodative amplitude of about 0.25 to about 8 diopters, or at least about 0.1, 0.2, 0.25, 0.5, 1, 1.2, 1.5, 1.8, 2, 2.5, 3, 5, or 8 diopters compared to the same lens before treatment.

Figure 7:
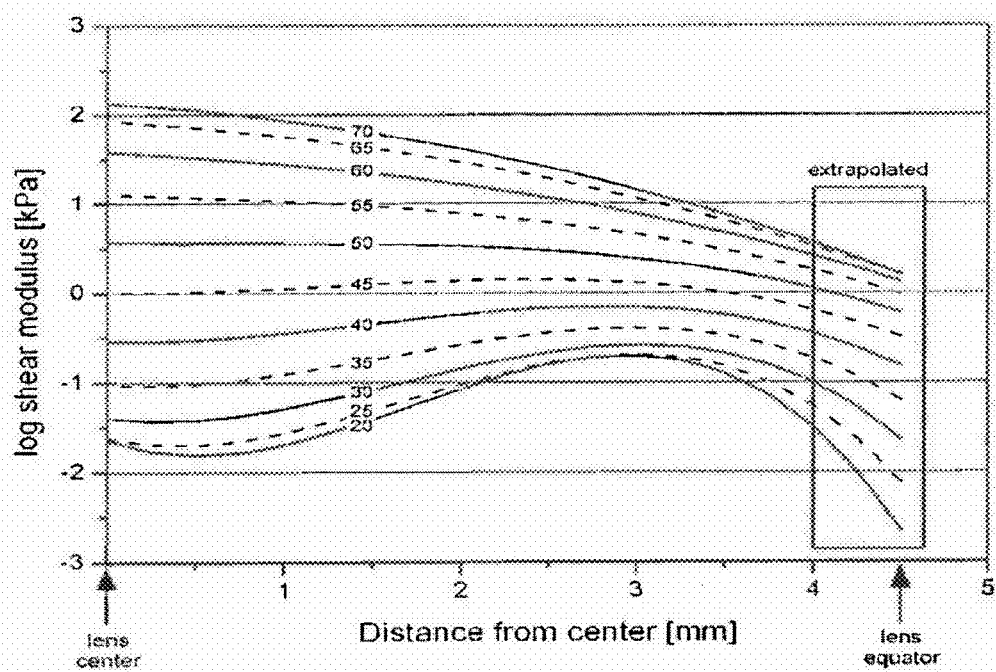
FIG. 7 shows a trend graph of the shear modulus versus position in the lens and age. Weeber, H A et al. 2007. Stiffness gradient in the crystalline lens. Graefes Arch Clin Exp Ophthalmol 245(9):1357-66. The line at the bottom is the 20-year-old lens; the line at the top is the 70-year-old lens. The modulus increases with age for all positions in the lens. Measurements were taken up to 4.0 mm from the lens centre. The lines are extrapolated to a radius of 4.5 mm (lens diameter 9.0 mm).

Lens elasticity can also be measured by the unit of elasticity E. The higher the value of E, the less elastic the lens. FIG. 7 depicts the average elasticity (E) of an untreated human lens as a function of age in years. In one embodiment, the agents or compounds described herein can decrease and/or maintain E at a value that is less than the E value exhibited by an untreated lens of about the same age. In other words, the agents or compounds can keep lens elasticity "below the line" depicted in FIG. 7. In one embodiment, E is decreased and/or maintained at a value about 2, 5, 7, 10, 15, 25, 50, 100, 150, or 200 percent below the line. However, as individual lenses may differ with respect to average values, another embodiment provides any increase in elasticity, maintenance of elasticity, or reduction in the rate of decline of elasticity (i.e., reduction in the rate of increase in E value) for an individual lens compared to the elasticity of the same lens before treatment.

Figure 8:
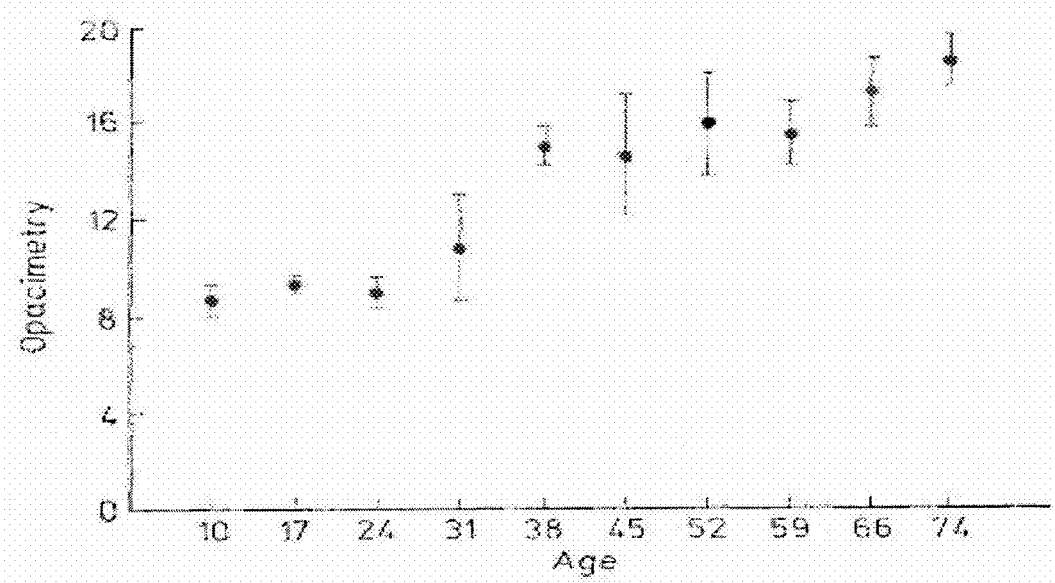
FIG. 8 depicts the average opacity (opacimetry) of an untreated human lens as a function of age in years. Bonomi, L et al. 1990. Evaluation of the 701 interzeag lens opacity meter. Graefe's Arch Clin Exp Ophthalmol 228(5):447-9. Lens opacity was measured in 73 healthy subjects between 10 and 76 years of age without slit-lamp evidence of cataract and with a visual acuity of 20/20. These subjects were classified into ten age groups. This study was carried out using the Interzeag Opacity Meter according to the procedure described by Flammer and Bebies (Flammer J, Bebie H. 1987. Lens Opacity Meter: a new instrument to quantify lens opacity. Ophthalmologica 195(2):69-72) and following the suggestions of the operating manual for the instrument.

Therapeutic efficacy can also be measured in terms of lens opacity. Lens opacity increases with age and is a primary diagnostic and causative factor for cataract. FIG. 8 depicts the average opacity of an untreated human lens as a function of age in years. In one embodiment, the agents or compounds described herein can decrease and/or maintain opacity at a value that is less than the opacity value exhibited by an untreated lens of about the same age. In other words, the agents or compounds can keep lens opacity "below the line" depicted in FIG. 8. In one embodiment, lens elasticity is decreased and/or maintained at a value about 2, 5, 7, 10, 15, 25, 50, 100, 150, or 200 percent below the line. However, as individual lenses may differ with respect to average values, another embodiment provides any decrease, maintenance, or reduction in the rate of increase of opacity for an individual lens compared to the opacity of the same lens before treatment.

Therapeutic efficacy can also be measured as a reduction in the rate of cell proliferation, particularly lens epithelial cell proliferation. Thus, in some embodiments, therapeutic efficacy can be measured by cytostatic effect.

Some agents or compounds described herein exist naturally in the untreated eye. Lipoic acid and cystine, for example, occur naturally in eye tissue. In general, a therapeutically effective amount of the exogenously administered agent is often at least about 1 or 2 orders of magnitude larger than the natural level of the agent. In one embodiment, the lipoic acid or derivative thereof is administered in a dose amount of up to about 1 mM. In one embodiment, the dose amount of lipoic acid or a derivative thereof is about 1 µM up to 1 mM, preferably about 0.25 mM to about 0.75 mM, or about 0.5 mM. In another embodiment, the dose amount of lipoic acid or derivative thereof is no more than 0.5 mM, 250 µM, 100 µM, 50 µM, 20 µM, or 10 µM. In another embodiment, cystine or a derivative thereof is administered in a dose amount of about 1 µM to about 20 µM. In yet another embodiment, the dose amount of cystine or a derivative thereof is no more than 20 µM, the limit of cystine solubility in aqueous solution, or no more than 15 µM, 12 µM, 10 µM, 7 µM, or 5 µM. The dose amount will depend on the route of administration as well as the age and condition of the patient. Similarly, the frequency of dosing will depend on similar factors as can be determined by one of ordinary skill in the art.

Efficacy has been demonstrated in vitro for specific exemplary dosing. FIG. 7 shows that the inelasticity increases by a factor of nearly 20 during the critical period from age 40 to 55 years. From current data, a 10 µM dose can decrease the inelasticity over 95% within a millimeter volume element (voxel). Extrapolation of these results to a volume element in the human lens suggests that using this treatment dose on a 55 year old person with a 10 kPA lens starting modulus value (see FIG. 7) could be reduced after treatment to a value of about 0.5 kPA (which then corresponds to a value typically seen with a 40 yr old person). FIG. 6 permits a conversion of these modulus values to optical amplitude: accommodative amplitude is normally reduced to almost 0 above 55 years, while a person at 40-45 years still exhibits around 4-5 diopters of accommodation.

The methods include preventative methods that can be performed on patients of any age. The methods also include therapeutic methods that can be performed on patients of any age, particularly patients that are at least 20, 25, 30, 35, 40, 45, 50, 52, 55, 57, 60, 70, 75, or 80 years of age.

The disclosures of all references and publications cited above are expressly incorporated by reference in their entireties.

Any numerical values recited herein include all values from the lower value to the upper value in increments of any measurable degree of precision. For example, if the value of a variable such as age, amount, time, percent increase/decrease and the like is 1 to 90, specifically from 20 to 80, and more specifically from 30 to 70, it is intended that values such as 15 to 85, 22 to 68, 43 to 51, 30.3 to 32, etc., are expressly enumerated in this specification. In other words, all possible combinations of numerical values between the lowest value and the highest value enumerated are to be considered to be expressly stated in this application in a similar manner.

Although particular features have been described with respect to particular embodiment as illustrative, one of ordinary skill in the art would recognize that any particular feature could be applied to any of the embodiments described herein. Various modifications and variations of the described agents or compounds, compositions, and methods will be apparent to those skilled in the art without departing from the scope and spirit of the invention. To further illustrate particular embodiments of the invention, we provide the following non-limiting examples.

EXAMPLES

Example 1

Synthesis of Cage:
4-Chloromethyl-7-hydroxy-2H-chromen-2-one (1)

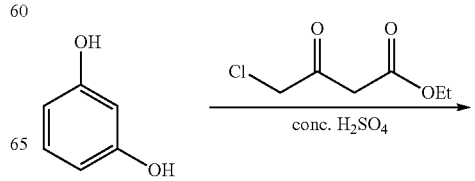

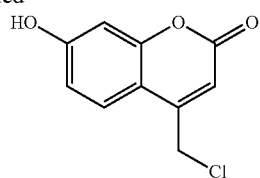

1

Ethyl 4-chloroacetoacetate (10.0 mL, 73.0 mmol) was added dropwise to a cold (ice bath) solution of resorcinol (8.0 g, 73.0 mmol) in concentrated $H_2SO_4$ (100 mL). The cooling bath was removed, and the reaction mixture was stirred at room temperature overnight (15 h), then poured onto ice (500 mL) and stirred until all ice had melted. The precipitate was collected by filtration and washed with water (200 mL). The solid was dissolved in hot EtOH:ligroin (4:1, 100 mL), filtered, and the filtrate was kept in the freezer (−20° C.) for 3 h. The solid was collected by filtration, washed with ligroin (3×10 mL), and dried to give 4-Chloromethyl-7-hydroxy-2H-chromen-2-one (1) as a pale white solid (12.2 g, 79%).

Example 2

Synthesis of Exemplary Caged Compound: (R)-(+)-(7-Hydroxy-2-oxo-2H-chromen-4-yl)methyl 5-(1,2-dithiolan-3-yl)pentanoate (2)

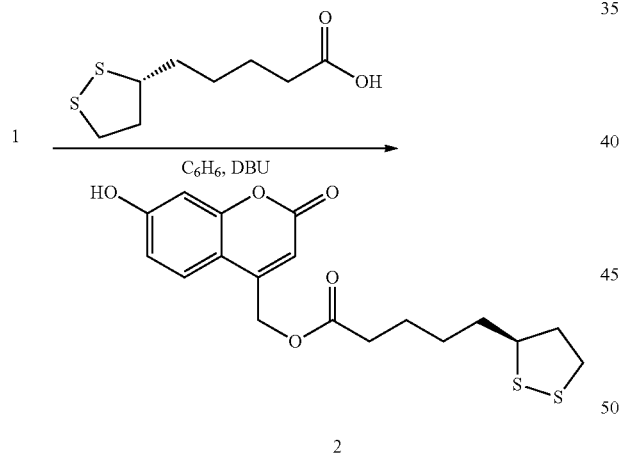

To a room temperature solution of (R)-(+)-1,2-dithiolane-3-pentanoic acid (2.66 g, 12.9 mmol) and 4-Chloromethyl-7-hydroxy-2H-chromen-2-one (1) (2.40 g, 11.4 mmol) in anhydrous benzene (160 mL) was added 1,8-diazabicyclo[5.4.0]undec-7-ene (3.8 mL, 25 mmol) in one portion. The reaction mixture was heated to 80° C. (oil bath temperature) for 1 h, cooled to room temperature, then quenched with aqueous 15% citric acid (200 mL). The resulting suspension was filtered, and the collected insoluble material was suspended in acetone (100 mL), sonicated for 60 s, then filtered onto a bed of silica gel (~10 g). The suspension-sonication-filtration step was repeated a second time. Concentration of the filtrate under reduced pressure followed by flash column chromatography (1% MeOH in $CH_2Cl_2$) provided the desired product as a pale yellow powder (1.08 g, 25%).

Example 3

Synthesis of Exemplary Caged Compound: 3,3'-Disulfanediylbis-((7-hydroxy-2-oxo-2H-chromen-4-yl)methoxy)-1-oxopropan-2-aminium chloride (3)

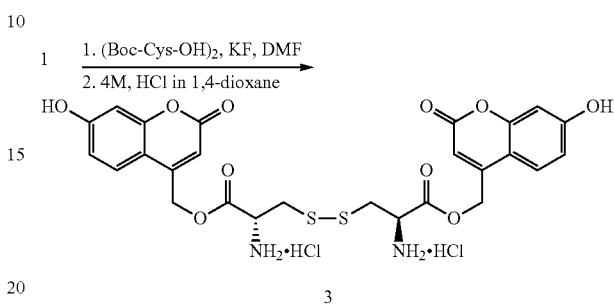

A solution of 1 (4.00 g, 19.0 mmol), (Boc-Cys-OH)$_2$ (2.60 g, 5.90 mmol), KF (2.06 g, 35.40 mmol), and anhydrous DMF (20 mL) was stirred at room temperature for 3 days. The mixture was concentrated, and the residue was dissolved in EtOAc (100 mL), washed with saturated aq. NaHCO3 (50 mL), brine (50 mL), and dried over MgSO$_4$. The drying agent was removed by filtration, and the filtrate was concentrated under reduced pressure. A suspension of the resulting orange solid (4.65 g, 5.90 mmol) in anhydrous $CH_2Cl_2$ (20 mL) and anhydrous 1,4-dioxane (40 mL) was treated with 4 M HCl in 1,4-dioxane (40 mL). The reaction mixture was stirred at room temperature for 16.5 h and concentrated under reduced pressure. Diethyl ether (200 mL) was added, and the resulting suspension was stirred for 30 min. The yellow solid was collected by filtration, washed with EtOAc and Et$_2$O, and dried in vacuo (3.21 g, 82% over 2 steps).

Example 4

Two-Photon Uncaging

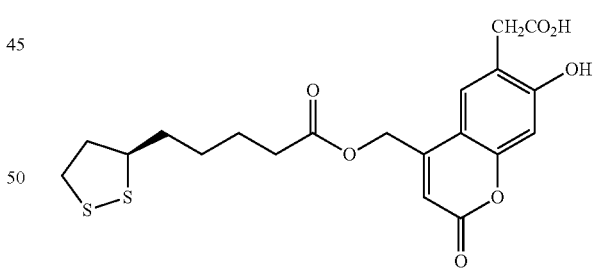

Figure 9:
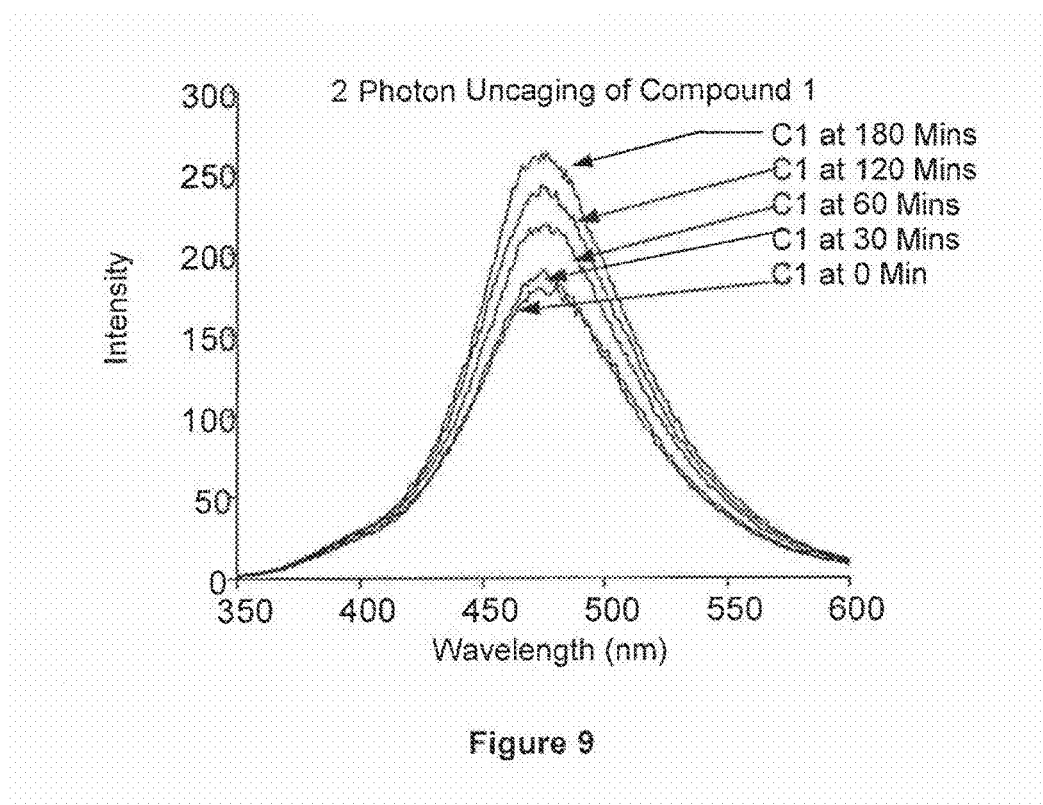
FIG. 9 plots wavelength versus intensity (maximal absorption at 470 nm) for the two-photon uncaging of an exemplary compound.
Figure 10:
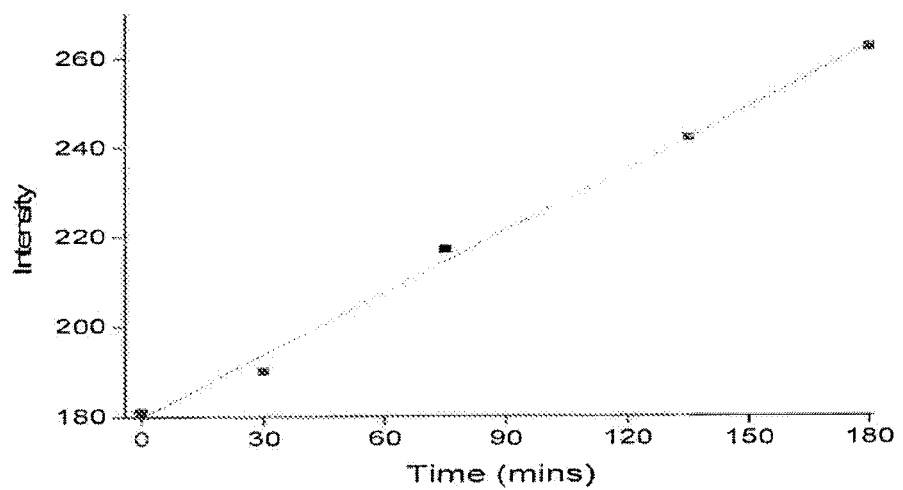
FIG. 10 plots time versus intensity and describes the uncaging linear rate constant for the two-photon uncaging of an exemplary compound.

60 µl of compound 1 was dissolved in 20:20 DMSO-methanol. Two-photon excitation from Ti-sapphire laser was used. Wavelength was set to 690 nm, and frequency doubler was used to get 345 excitation for uncaging compound 1. Lazing power was approximately 0.75 mwatts. See FIGS. 9 and 10.

Example 5

In Vitro Toxicology Studies

Cell viability was determined using human umbilical vein endothelial cells (HUVEC, first passage). Cells were treated with the active agent, the caged active agent, and the photoproduct of the cage in doses ranging from 0.1 μM to 100 μM. The number of live and dead cells was determined using the MultiTox-Fluor assay (Promega) or Live/Dead® assay (Invitrogen). Logistic plots were used to determine each compound's $LD_{50}$ value. Lipoic acid was not cytotoxic in the concentration range. The cage photoproduct, 4-hydroxymethyl-7-hydroxycoumarin, had an $LD_{50}$ of 46 μM. The 7-hydroxymethyl-caged lipoic acid had an LD50 of 10.76 μM.

Example 6

In Vitro Efficacy Studies

Increase in Elasticity:
Pairs of mouse lenses were incubated in medium 200 supplemented with an antibiotic, an antimycotic, in the presence or absence of lipoic acid (concentrations ranging from 0.5 μM to 500 μM) for 8-15 hours. Each lens was removed from medium, weighed, and photographed on a micrometer scale. A coverslip of known weight (0.17899±0.00200 g) was placed on the lens, and the lens was photographed again on the micrometer scale. The diameter of each lens with and without the coverslip was determined from the photographs. The change in lens diameter produced by the force (coverslip) was computed $\Delta D=(D_{withcoverslip}-D_{withoutcoverslip})$. The results (FIG. 11, ‡) indicate that lipoic acid at concentrations≥9.6 μM caused a statistically significant increase in ΔD, p<0.0001.

Figure 11:
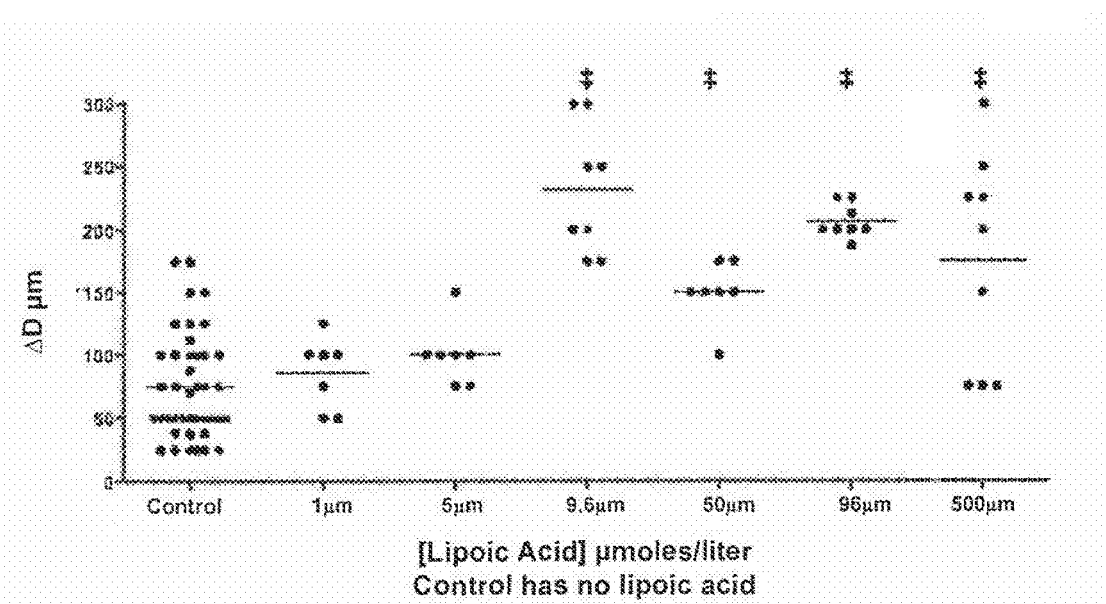
FIG. 11 depicts a scatter plot of the change in ΔD (micrometers) in the absence (control) and presence of lipoic acid in lens organ culture experiments. The symbol ‡ designates significantly larger changes in ΔD when compared to controls. Statistical values are highly significant at p<0.0001 by unpaired t-test and by Kruskal Wallis test, which compared medians of each data set. The relative change in Young's modulus (E) can be calculated as the cubic value derived from the ΔD of the control divided by the ΔD of the experimental or E fractional change=(ΔD con/ΔDexp)^3.
Figure 12:
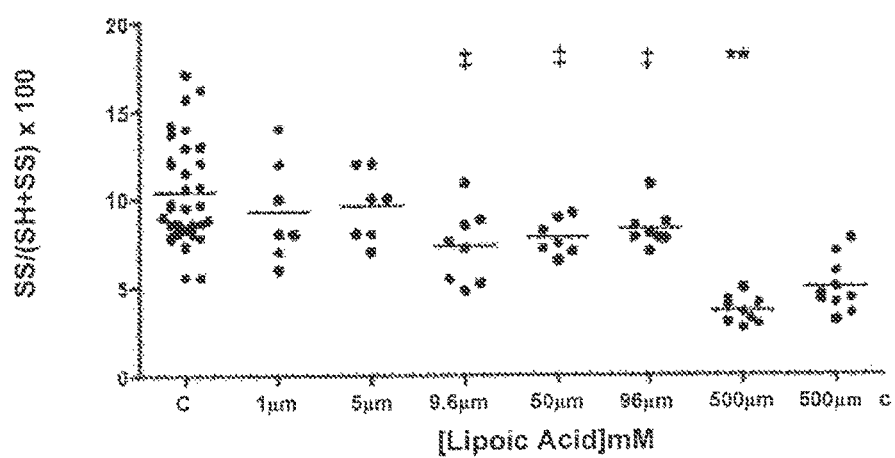
FIG. 12 depicts a scattergram of the percent of the total protein SH groups in disulfide bonds. Free SH groups were alkylated with 4-acetamido-4'-maleimidylstilbene-2,2'-sulfonic acid (c, 1 μM, 5 μM, 9.6 μM, 50 μM, 96 μM) or 7-diethylamino-3-(4' maleimidylphenyl)-4-methyl coumarin (500 μM, and 500 μM c). Following removal of the first alkylating agent, the S—S bonds were reduced and alkylated with fluorescein-5-maleimide. Absorption spectra were used to calculated total protein (A280 nm), free protein SH (A322 or A384), and protein SS (A490) using the appropriate extinction coefficients. The symbol ‡ indicates statistically significant difference of mean with mean of control (c, p≤0.05). The symbol ** indicates means of 500 μM lipoic acid and the 500 μM control were significantly different from each other (p=0.027).

Decrease in Disulfide Bonds:
Lipoic acid at concentrations≥9.6 μM caused a statistically significant decrease in protein disulfides in the mouse lenses where there was a significant increase in ΔD (FIG. 11). Mouse lenses were homogenized in a denaturing buffer containing a fluorescent alkylating agent to modify the free SH groups. After removing the alkylating agent homogenates were reduced and alkylated with a different fluorescent alkylating agent. Absorption spectra of the modified proteins were used to calculate free protein SH and protein SS groups. The results are shown in FIG. 12.

Example 7

Preclinical and Clinical Studies

An exemplary clinical protocol may include patient selection criteria of age 45-55 years with some loss of clinical accommodative amplitude.

A test compound and/or placebo control may be administered in a controlled dark sterile environment with 1-photon visible light LED (computer controlled tilt mirror) system.

For acute treatment, the clinician could 1) apply a topical mydriatic agent, 2) wait for pupillary dilatation (about 5 minutes), 3) introduce a test compound and/or placebo control with an appropriate delivery device, 4) wait 30 minutes, 5) apply visible wavelength laser or UVA (~365 nm) spatial (voxel) activation to release active agent from the caged compound in a target lens region (5 minutes), and 6) apply topical agent (e.g., cholecystokinin and vasopressin) to retract iris sphincter muscle to aid release of zonular tension during lens cytosol protein remolding.

Immediately following the procedure, the clinician may allow a time period for ocular drug clearance (e.g., about 30-60 minutes) and then allow patient to go home with laser glasses having a cutoff filter of about >550 nm.

For post-operative follow-up in about 1 day to 1 week, the clinician may evaluate the treatment modality for a desired visual endpoint, e.g., accommodative amplitude or elasticity.

The procedure can be repeated to gain further efficacy (e.g., to obtain 2 D in patients older than 55 years) and/or to restore near vision (depending on the duration of action).

A similar protocol could be adapted for preclinical testing animal in vivo lens models.

The examples given above are merely illustrative and are not meant to be an exhaustive list of all possible embodiments, applications, or modifications of the invention. Thus, various modifications and variations of the described methods and systems of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes of carrying out the invention which are obvious to those skilled in the chemical arts or in the relevant fields are intended to be within the scope of the appended claims.

The disclosures of all references and publications cited above are expressly incorporated by reference in their entireties to the same extent as if each were incorporated by reference individually.

What is claimed is:

1. A pharmaceutical composition comprising an agent for treating presbyopia having a formula:

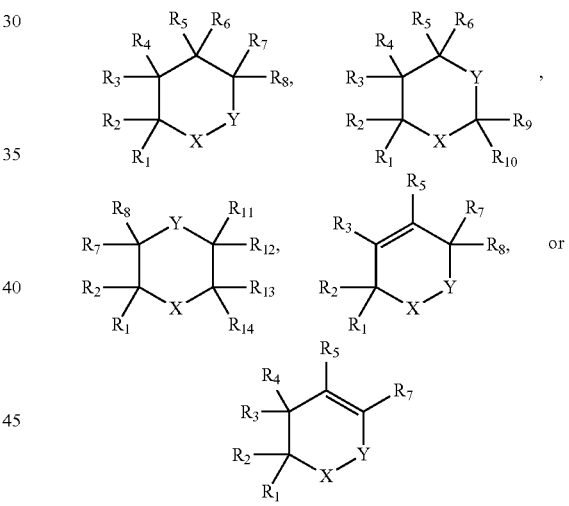

wherein at least one of X and Y is sulfur, and the other is sulfur, selenium, or a sulfonic group, and
each R group is independently selected from the group consisting of: —H, —OH, —OAc, —OR, —SR, —CO$_2$R, an electron withdrawing group, and a linear or branched $C_{1-18}$ alkane or alkene optionally substituted by one or more substituents selected from the group consisting of ether, ester, carboxylic acid, phosphate, amide, and amine groups; and a pharmaceutically acceptable carrier.

2. The pharmaceutical composition of claim 1, wherein in the formula of the agent, X and Y are both sulfur.

3. The pharmaceutical composition of claim 1, wherein in the formula of the agent, one of X and Y is sulfur, and the other is sulfur or selenium.

4. The pharmaceutical composition of claim 1, wherein in the formula of the agent, at least one of $R_{1-14}$ is —OH or —OAc.

5. The pharmaceutical composition of claim 4, wherein the agent has the formula:

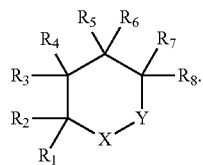

6. The pharmaceutical composition of claim 5, wherein the agent has a formula:

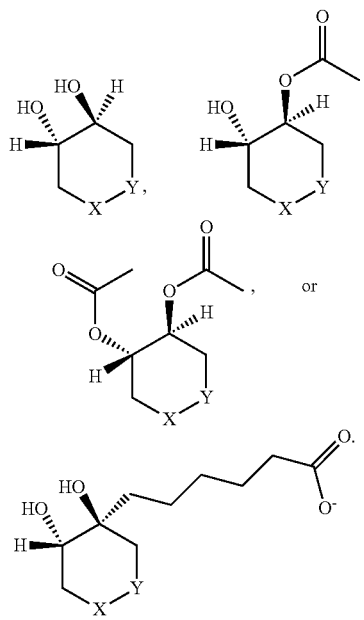

7. The pharmaceutical composition agent of claim 1, wherein in the formula of the agent, at least one of $R_{1-14}$ is a linear substituent selected from the group consisting of $C_{2-10}$ alkane and $C_{10-18}$ alkene.

8. The pharmaceutical composition of claim 7, wherein in the formula of the agent, the linear substituent has a distal terminal that is —COOH, —NH$_2$, —CO$_2$CH$_3$, or —CO$_2$CH$_2$CH$_3$.

9. The pharmaceutical composition of claim 8, wherein in the formula of the agent, the linear substituent is —(CH$_2$)$_{2-10}$NH$_2$.

10. The pharmaceutical composition of claim 8, wherein in the formula of the agent, the linear substituent is —(CH$_2$)$_{2-10}$CO$_2$H.

11. The pharmaceutical composition of claim 1, wherein the agent has a formula:

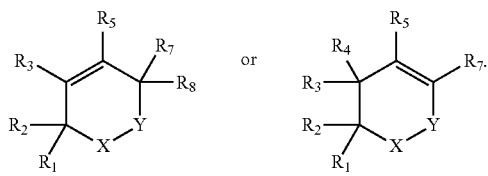

12. The pharmaceutical composition of claim 11, wherein the agent has a formula:

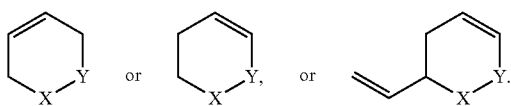

13. A pharmaceutical composition comprising an agent for treating presbyopia having a formula:

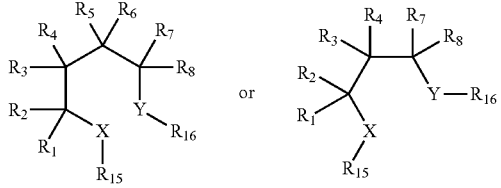

wherein at least one of X and Y is sulfur, and the other is sulfur, selenium, or a sulfonic group, and wherein each R group is independently selected from the group consisting of: —H, —OH, —OAc, —OR, —SR, —CO$_2$R, an electron withdrawing group, and a linear or branched C$_{1-18}$ alkane or alkene optionally substituted by one or more substituents selected from the group consisting of ether, ester, carboxylic acid, phosphate, amide, and amine groups; and a pharmaceutically acceptable carrier.

14. A pharmaceutical composition comprising an agent for treating presbyopia having a formula:

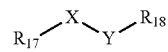

wherein at least one of X and Y is sulfur, and the other is sulfur, selenium, or a sulfonic group, and each R group is independently selected from the group consisting of: —H, —OH, —OAc, —OR, —SR, —CO$_2$R, an electron withdrawing group, and a linear or branched C$_{1-18}$ alkane or alkene optionally substituted by one or more substituents selected from the group consisting of ether, ester, carboxylic acid, phosphate, amide, and amine groups; and a pharmaceutically acceptable carrier.

15. The pharmaceutical composition of claim 14, wherein the agent is:

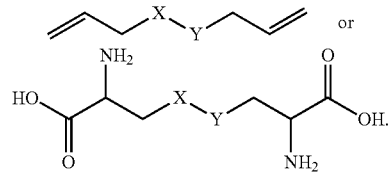

16. A pharmaceutical composition for ocular use, comprising:
cystine or derivative thereof, optionally caged by a photolabile protecting group; and a pharmaceutically acceptable carrier.

17. The pharmaceutical composition of claim 16, wherein the active agent is caged by a photolabile protecting group.

18. A method of treating presbyopia, comprising administering the pharmaceutical composition of claim 1 to a subject in need thereof.

19. A method of treating presbyopia, comprising administering the pharmaceutical composition of claim 13 to a subject in need thereof.

20. A method of treating presbyopia, comprising administering the pharmaceutical composition of claim 14 to a subject in need thereof.

* * * * *